(12) United States Patent
Muller

(10) Patent No.: US 8,409,189 B2
(45) Date of Patent: Apr. 2, 2013

(54) SYSTEM AND METHOD FOR RESHAPING AN EYE FEATURE

(75) Inventor: David Muller, Boston, MA (US)

(73) Assignee: Avedro, Inc., Waltham, MA (US)

( * ) Notice: Subject to any disclaimer, the term of this patent is extended or adjusted under 35 U.S.C. 154(b) by 1102 days.

(21) Appl. No.: 12/018,457

(22) Filed: Jan. 23, 2008

(65) Prior Publication Data

US 2009/0187184 A1 Jul. 23, 2009

(51) Int. Cl.
*A61B 18/14* (2006.01)

(52) U.S. Cl. ............................ 606/34; 606/41

(58) Field of Classification Search ............... 606/3–7, 606/10–20, 22–41; 604/20; 607/53; 198/898
See application file for complete search history.

(56) References Cited

U.S. PATENT DOCUMENTS

| | | | |
|---|---|---|---|
| 3,776,230 A | 12/1973 | Neefe | |
| 4,326,529 A | 4/1982 | Doss et al. | |
| 4,381,007 A | 4/1983 | Doss | |
| 4,490,022 A | 12/1984 | Reynolds | |
| 4,546,773 A * | 10/1985 | Kremer et al. | 600/452 |
| 4,712,543 A | 12/1987 | Baron | |
| 4,743,725 A | 5/1988 | Risman | |
| 4,796,623 A * | 1/1989 | Krasner et al. | 606/166 |
| 4,805,616 A | 2/1989 | Pao | |
| 4,881,543 A | 11/1989 | Trembly et al. | |
| 4,891,043 A | 1/1990 | Zeimer et al. | |
| 4,943,296 A | 7/1990 | Funakubo et al. | 606/166 |
| 4,994,058 A | 2/1991 | Raven et al. | |
| 5,103,005 A | 4/1992 | Gyure et al. | |
| 5,171,254 A | 12/1992 | Sher | |
| 5,281,211 A | 1/1994 | Parel et al. | |
| 5,332,802 A | 7/1994 | Kelman et al. | |
| 5,370,644 A | 12/1994 | Langberg | |
| 5,395,385 A * | 3/1995 | Kilmer et al. | 606/166 |
| 5,437,658 A | 8/1995 | Muller et al. | |

(Continued)

FOREIGN PATENT DOCUMENTS

| | | |
|---|---|---|
| EP | 1 561 440 | 8/2005 |
| EP | 1 790 383 | 5/2007 |

(Continued)

OTHER PUBLICATIONS

International Search Report for PCT/US09/31718, dated Mar. 4, 2009.

(Continued)

*Primary Examiner* — Michael Peffley
*Assistant Examiner* — Khadijeh Vahdat
(74) *Attorney, Agent, or Firm* — Nixon Peabody LLP

(57) ABSTRACT

A system for applying therapy to an eye includes an applicator having a conducting element configured to direct energy from an energy source to an application end of the conducting element, where the application end has an eye contact portion. A positioning system receives the applicator and positions the eye contact portion in stable engagement with the surface of an eye. In some embodiments, the conducting element is disposed within a housing for the applicator and an adjustment system is employed to move the conducting element relative to the housing. The adjustment system enables controlled movement of the conducting element and the eye contact portion against the corneal surface. In particular embodiments, sufficient contact between the applicator and the cornea is determined by causing applanation of the cornea. In other embodiments, a physical measurement device, such as a strain gauge, is employed to determine when sufficient contact has been established.

31 Claims, 12 Drawing Sheets

U.S. PATENT DOCUMENTS

| | | | |
|---|---|---|---|
| 5,461,212 A | 10/1995 | Seiler et al. | |
| 5,490,849 A | 2/1996 | Smith | |
| 5,586,134 A | 12/1996 | Das et al. | |
| 5,618,284 A | 4/1997 | Sand | |
| 5,624,456 A * | 4/1997 | Hellenkamp | 606/166 |
| 5,634,921 A | 6/1997 | Hood et al. | |
| 5,658,278 A | 8/1997 | Imran et al. | |
| 5,766,171 A | 6/1998 | Silvestrini | |
| 5,779,696 A | 7/1998 | Berry et al. | |
| 5,814,040 A | 9/1998 | Nelson et al. | |
| 5,830,139 A | 11/1998 | Abreu | |
| 5,873,901 A | 2/1999 | Wu et al. | |
| 5,885,275 A | 3/1999 | Muller | |
| 5,910,110 A | 6/1999 | Bastable | |
| 5,919,222 A | 7/1999 | Hjelle et al. | |
| 6,033,396 A | 3/2000 | Huang et al. | |
| 6,053,909 A | 4/2000 | Shadduck | |
| 6,104,959 A | 8/2000 | Spertell | |
| 6,139,876 A | 10/2000 | Kolta | |
| 6,149,646 A | 11/2000 | West, Jr. et al. | |
| 6,161,544 A | 12/2000 | DeVore et al. | |
| 6,162,210 A | 12/2000 | Shadduck | |
| 6,293,938 B1 | 9/2001 | Muller | |
| 6,319,273 B1 | 11/2001 | Chen et al. | |
| 6,325,792 B1 | 12/2001 | Swinger et al. | |
| 6,334,074 B1 | 12/2001 | Spertell | |
| 6,342,053 B1 | 1/2002 | Berry | |
| 6,402,739 B1 | 6/2002 | Neev | |
| 6,413,255 B1 | 7/2002 | Stern | |
| 6,520,956 B1 | 2/2003 | Huang | |
| 6,617,963 B1 | 9/2003 | Watters et al. | |
| 6,749,604 B1 | 6/2004 | Eggers et al. | |
| 6,946,440 B1 | 9/2005 | DeWoolfson et al. | |
| 7,044,945 B2 | 5/2006 | Sand | |
| 7,130,835 B2 | 10/2006 | Cox et al. | |
| 7,141,049 B2 | 11/2006 | Stern et al. | |
| 7,192,429 B2 | 3/2007 | Trembly | |
| 7,270,658 B2 | 9/2007 | Woloszko et al. | |
| 7,402,562 B2 | 7/2008 | DeWoolfson | |
| 7,713,268 B2 | 5/2010 | Trembly | |
| 2001/0034502 A1* | 10/2001 | Moberg et al. | 604/154 |
| 2002/0002369 A1 | 1/2002 | Hood | |
| 2002/0013579 A1 | 1/2002 | Silvestrini | |
| 2002/0035345 A1 | 3/2002 | Beck | 604/20 |
| 2002/0049437 A1 | 4/2002 | Silvestrini | |
| 2002/0077699 A1* | 6/2002 | Olivieri et al. | 623/5.11 |
| 2002/0099363 A1 | 7/2002 | Woodward et al. | |
| 2002/0164379 A1 | 11/2002 | Nishihara et al. | |
| 2003/0018255 A1 | 1/2003 | Martin et al. | |
| 2003/0097130 A1 | 5/2003 | Muller et al. | |
| 2003/0175259 A1 | 9/2003 | Karageozian | |
| 2003/0216728 A1* | 11/2003 | Stern et al. | 606/41 |
| 2004/0001821 A1 | 1/2004 | Silver et al. | |
| 2004/0002640 A1 | 1/2004 | Luce | 600/399 |
| 2004/0111086 A1 | 6/2004 | Trembly | |
| 2004/0143250 A1 | 7/2004 | Trembly | |
| 2004/0199158 A1 | 10/2004 | Hood et al. | |
| 2004/0243160 A1 | 12/2004 | Shiuey et al. | |
| 2005/0033202 A1 | 2/2005 | Chow et al. | |
| 2005/0070977 A1 | 3/2005 | Molina | |
| 2005/0183732 A1 | 8/2005 | Edwards | 128/898 |
| 2005/0197657 A1 | 9/2005 | Goth et al. | |
| 2005/0287217 A1 | 12/2005 | Levin et al. | |
| 2006/0135957 A1 | 6/2006 | Panescu | |
| 2006/0149343 A1 | 7/2006 | Altshuler et al. | |
| 2006/0189964 A1 | 8/2006 | Anderson et al. | |
| 2006/0206110 A1 | 9/2006 | Knowlton et al. | |
| 2006/0254851 A1 | 11/2006 | Karamuk | |
| 2006/0287649 A1 | 12/2006 | Ormsby et al. | 606/33 |
| 2006/0287662 A1 | 12/2006 | Berry et al. | |
| 2007/0048340 A1 | 3/2007 | Ferren et al. | |
| 2007/0055227 A1 | 3/2007 | Khalaj et al. | |
| 2007/0074722 A1 | 4/2007 | Giroux et al. | |
| 2007/0114946 A1 | 5/2007 | Goetze et al. | |
| 2007/0123845 A1 | 5/2007 | Lubatschowski | |
| 2007/0161976 A1 | 7/2007 | Trembly | |
| 2007/0179564 A1 | 8/2007 | Harold | |
| 2007/0203547 A1 | 8/2007 | Costello et al. | |
| 2007/0244470 A1 | 10/2007 | Barker et al. | |
| 2007/0244496 A1 | 10/2007 | Hellenkamp | |
| 2008/0015660 A1 | 1/2008 | Herekar | |
| 2008/0027328 A1 | 1/2008 | Klopotek et al. | |
| 2009/0024117 A1 | 1/2009 | Muller | |
| 2009/0054879 A1 | 2/2009 | Berry | |
| 2009/0069798 A1 | 3/2009 | Muller et al. | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0187173 A1 | 7/2009 | Muller | |
| 2009/0209954 A1 | 8/2009 | Muller et al. | |
| 2010/0094197 A1 | 4/2010 | Marshall et al. | |

FOREIGN PATENT DOCUMENTS

| | | |
|---|---|---|
| EP | 2 269 531 | 1/2011 |
| WO | WO 99/17690 | 4/1999 |
| WO | WO 00/09027 | 2/2000 |
| WO | 0074648 A2 | 12/2000 |
| WO | WO 2004/052223 | 6/2004 |
| WO | 2006/128038 A2 | 11/2006 |
| WO | WO 2007/022993 | 3/2007 |
| WO | 2007/120457 A2 | 10/2007 |
| WO | WO 2009/012490 | 1/2009 |
| WO | WO 2009/073213 | 6/2009 |
| WO | WO 2009/094467 | 7/2009 |
| WO | WO 2010/039854 | 4/2010 |
| WO | WO 2011/050164 | 4/2011 |

OTHER PUBLICATIONS

Written Opinion of the International Searching Authority for PCT/US09/31718, dated Mar. 4, 2009.
Alain Chandonnet et al., "CO2 Laser Annular Thermokeratoplasty: A Preliminary Study", Lasers in Surgery and Medicine 12:264-273 (1992), Wiley-Lill, Inc., pp. 264-273.
International Search Report for PCT/US08/76062, dated Nov. 7, 2008, 3 pages.
Written Opinion of the International Searching Authority for PCT/US08/76062, dated Nov. 7, 2008, 7 pages.
Berjano et al.; "Radio-Frequency Heating of the Cornea: Theoretical Model and In Vitro Experiments"; IEEE Transactions on Biomedical Engineering; vol. 49; No. 3; Mar. 2002; pp. 196-205.
Berjano et. al.; "Ring Electrode for Radio-Frequency Heating of the Cornea: Modelling and in Vitro Experiments"; Medical & Biological Engineering & Computing 2003; vol. 41; pp. 630-639.
International Search Report mailed Aug. 14, 2009 for PCT/US2009/042204, (5 pages).
International Search Report mailed Nov. 20, 2009 for PCT/US2009/059061 (3 pages).
International Search Report mailed Nov. 6, 2009 for PCT/US2009/057481 (2 pages).
International Search Report for PCT/US2010/029806 dated Jun. 1, 2010 (3 pages).
Written Opinion for PCT/US2010/029806 dated Jun. 1, 2010 (6 pages).
International Search Report for PCT/US2010/029791 dated Jun. 1, 2010 (3 pages).
Written Opinion for PCT/US2010/029791 dated Jun. 1, 2010 (6 pages).
Trembly et al.; Microwave Thermal Keratoplasty for Myopia: Keratoscopic Evaluation in Procine Eyes; Journal of Refractive Surgery; vol. 17; Nov./Dec. 2001; (8 pages).
Muller et al., Br. J. Opthalmol 2001; 85:437-443 (April).
Naoumidi et al., J. Cataract Refract Surg. May 2006; 32(5):732-41.
Pallikaris et al., J. Cataract Refract Surg. Aug. 2005; 31(8):1520-29.
Acosta et al., Cornea. Aug. 2006;25(7):830-8.
European Search Report and Written Opinion for EP 08799473.7, European Patent Office, dated May 24, 2011 (6 pages).
Search Report corresponding to International Patent Application Serial No. PCT/US2009/031718, United States Patent Office; dated Mar. 4, 2009 (2 pages).
Written Opinion corresponding to International Patent Application Serial No. PCT/ U52009/031718, United States Patent Office; dated Mar. 4, 2009 (5 pages).

Alió JL, Amparo F, Ortiz D, Moreno L, "Corneal Multifocality With Excimer Laser for Presbyopia Correction," *Current Opinion in Ophthalmology*, vol. 20, Jul. 2009, pp. 264-271 (8 pages).
Alió JL, Chaubard JJ, Caliz A, Sala E, Patel S, "Correction of Presbyopia by Technovision Central Multifocal LASIK (PresbyLASIK)," *Journal of Refractive Surgery*, vol. 22, May 2006, pp. 453-460 (8 pages).
Anderson K, El-Sheikh A, Newson T, "Application of Structural Analysis to the Mechanical Behavior of the Cornea," *Journal of the Royal Society Interface*, vol. 1, May 2004, pp. 3-15 (13 pages).
Andreassen TT, Simonsen Ah, Oxlund H, "Biomechanical Properties of Keratoconus and Normal Corneas," *Experimental Eye Research*, vol. 31, Oct. 1980, pp. 435-441 (7 pages).
Anschutz T, "Laser Correction of Hyperopia and Presbyopia," *International Ophthalmology Clinics*, vol. 34, No. 4, Fall 1994, pp. 107-137 (33 pages).
Bailey MD, Zadnik K, "Outcomes of LASIK for Myopia With FDA-Approved Lasers," *Cornea*, vol. 26, No. 3, Apr. 2007, pp. 246-254 (9 pages).
Borja D, Manns F, Lamar P, Rosen A, Fernandez V, Parel TM, "Preparation and Hydration Control of Corneal Tissue Strips for Experimental Use," *Cornea*, vol. 23, No. 1, Jan. 2004, pp. 61-66 (7 pages).
Bower KS, Weichel ED, Kim TJ, "Overview of Refractive Surgery," *Am Fam Physician*, vol. 64, No. 7, Oct. 2001, pp. 1183-1190 (8 pages).
Braun EH, Lee J, Steinert RF, "Monovision in LASIK," *Ophthalmology*, vol. 115, No. 7, Jul. 2008, pp. 1196-1202 (7 pages).
Bryant MR, Marchi V, Juhasz T, "Mathematical Models of Picosecond Laser Keratomileusis for High Myopia," *Journal of Refractive Surgery*, vol. 16, No. 2, Mar.-Apr. 2000, pp. 155-162 (9 pages).
Bryant MR, McDonnell PJ, "Constitutive Laws for Biomechanical Modeling of Refractive Surgery," *Journal of Biomechanical Engineering*, vol. 118, Nov. 1996, pp. 473-481 (10 pages).
Buzard KA, Fundingsland BR, "Excimer Laser Assisted in Situ Keratomileusis for Hyperopia," *Journal of Cataract & Refractive Surgery*, vol. 25, Feb. 1999, pp. 197-204 (8 pages).
Charman WN, "The Eye in Focus: Accommodation and Presbyopia," *Clinical and Experimental Optometry*, vol. 91, May 2008, pp. 207-225 (19 pages).
Corbett et al, "Effect of Collagenase Inhibitors on Coreal Haze after PRK", Exp. Eye Res., vol. 72, Issue 3, pp. 253-259, dated Jan. 29, 2001 (7 pages).
Cox CA, Krueger RR, "Monovision with Laser Vision Correction," *Ophthalmology Clinics of North Amermica*, vol. 19, No. 1, Mar. 2006, pp. 71-75 (7 pages).
Doss JD, Albillar JI, "A Technique for the Selective Heating of Corneal Stroma," *Contact & Intraocular Lens Medical Journal*, vol. 6, No. 1, Jan.-Mar. 1980, pp. 13-17 (8 pages).
Elsheikh A, Anderson K, "Comparative Study of Corneal Strip Extensometry and Inflation Tests," *Journal of the Royal Society Interface*, vol. 2, May 2005, pp. 177-185 (10 pages).
Evans BJW, "Monovision: a Review," *Ophthalmic and Physiological Optics*, vol. 27, Jan. 2007, pp. 417-439 (23 pages).
Gasset AR, Kaufman HE, "Thermokeratoplasty in the Treatment of Keratoconus," *American Journal of Ophthalmology*, vol. 79, Feb. 1975, pp. 226-232 (8 pages).
Gloster J, Perkins ES, "The Validity of the Imbert-Flick Law as Applied to Applanation Tonometry," *Experimental Eye Research*, vol. 2, Jul. 1963, pp. 274-283 (10 pages).
Gupta N, Naroo SA, "Factors Influencing Patient Choice of Refractive Surgery or Contact Lenses and Choice of Centre," *Contact Lens & Anterior Eye*, vol. 29, Mar. 2006, pp. 17-23 (7 pages).
Hamilton DR, Hardten DR, Lindstrom RL, "Thermal Keratoplasty," *Cornea*, 2$^{nd}$ Edition, Chapter 167, 2005, pp. 2033-2045 (13 pages).
Hersh PS, "Optics of Conductive Keratoplasty: Implication for Presbyopia Management," *Transactions of the American Ophthalmological Society*, vol. 103, 2005, pp. 412-456 (45 pages).
Hjortdal JO, "Extensibility of the Normo-Hydrated Human Cornea," *Acta Ophthalmologica Scandinavica*, vol. 73, No. 1, Feb. 1995, pp. 12-17 (7 pages).

Hori-Komai Y, Toda I, Asano-Kato N, Tsubota K, "Reasons for Not Performing Refractive Surgery," *Journal of Cataract & Refractive Surgery*, vol. 28, May 2002, pp. 795-797 (3 pages).
Illueca C, Alió JL, Mas D, Ortiz D, Pérez J, Espinosa J, Esperanza S, "Pseudoaccommodation and Visual Acuity with Technovision PresbyLASIK and a Theoretical Simulated Array® Multifocal Intraocular Lens," *Journal of Refractive Surgery*, vol. 24, Apr. 2008, pp. 344-349 (6 pages).
Jain S, Arora I, Azar DT, "Success of Monovision in Presbyopes: Review of the Literature and Potential Applications to Refractive Surgery," *Survey of Ophthalmology*, vol. 40, No. 6, May-Jun. 1996, pp. 491-499 (9 pages).
Jin GJC, Lyle A, Merkley KH, "Laser in Situ Keratomileusis for Primary Hyperopia," *Journal of Cataract & Refractive Surgery*, vol. 31, Apr. 2005, pp. 776-784 (9 pages).
Kaliske M, "A Formulation of Elasticity and Viscoelasticity for Fibre Reinforced Material at Small and Finite Strains," *Computer Methods in Applied Mechanics and Engineering*, vol. 185, 2000, pp. 225-243 (19 pages).
Llovet F, Galal A, Benitez-del-Castillo J-M, Ortega J, Martin C, Baviera J, "One-Year Results of Excimer Laser in Situ Keratomileusis for Hyperopia," *Journal of Cataract & Refractive Surgery*, vol. 35, Jul. 2009, pp. 1156-1165 (10 pages).
Loarie TM, Applegate D, Kuenne CB, Choi LJ, Horowitz DP, "Use of Market Segmentation to Identify Untapped Consumer Needs in Vision Correction Surgery for Future Growth," *Journal of Refractive Surgery*, vol. 19, No. 5, Sep.-Oct. 2003, pp. 566-576 (12 pages).
Maxwell WA, Lane SS, Zhou F, "Performance of Presbyopia-Correcting Intraocular Lenses in Distance Optical Bench Tests," *Journal of Cataract & Refractive Surgery*, vol. 35, Jan. 2009, pp. 166-171 (6 pages).
McDonald MB, Durrie D, Asbell P, Maloney R, Nichamin L, "Treatment of Presbyopia With Conductive Keratoplasty: Six-Month Results of the 1-Year United States FDA Clinical Trial," *Cornea*, vol. 23, No. 7, Oct. 2004, pp. 661-668 (8 pages).
McDonald MB, "Conductive Keratoplasty: a Radiofrequency-Based Technique for the Correction of Hyperopia," *Transactions of the American Ophthalmological Society*, vol. 103, Dec. 2005, pp. 512-536 (25 pages).
Moriera MD, Garbus JJ, Fasano A, Lee M, Clapham TN, McDonnel PJ, "Multifocal Corneal Topographic Changes With Excimer Laser Photorefractive Keratectomy," *Archives of Ophthalmology*, vol. 110, Jul. 1992, pp. 994-999 (6 pages).
Nash IS, Greene PR, Foster CS, "Comparison of Mechanical Properties of Keratoconus and Normal Corneas," *Experimental Eye Research*, vol. 35, 1982, pp. 413-424 (12 pages).
Newman JM, "Analysis, Interpretation, and Prescription for the Ametropias and Heterophorias," *Borish's Clinical Refraction*, 1998, pp. 776-822 (49 pages).
Pandolfi A, Manganiello F, "A Model for the Human Cornea: Formulation and Numerical Analysis," *Biomechanics and Modeling in Mechanobiology*, vol. 5, Jan. 2006, pp. 237-246 (10 pages).
Pertaub R, Ryan TP, "Numerical Model and Analysis of an Energy-Based System Using Microwaves for Vision Correction," *Proceedings of SPIE*, vol. 7181, Feb. 2009, p. 718105-1 to 718105-14 (14 pages).
Petroll WM, Roy P, Chuong CJ, Hall B, Cavanagh HD, Jester JV, "Measurement of Surgically Induced Corneal Deformations Using Three-Dimensional Confocal Microscopy," *Cornea*, vol. 15, No. 2, Mar. 1996, pp. 154-164 (12 pages).
Pinelli R, Ortiz D, Simonetto A, Bacchi C, Sala E, Alió JL, "Correction of Presbyopia in Hyperopia With a Center-Distance Paracentral-Near Technique Using the Technolas 217Z Platform," *Journal of Refractive Surgery*, vol. 24, May 2008, pp. 494-500 (7 pages).
Pinsky PM, Datye DV, "A Microstructurally-Based Finite Element Model of the Incised Human Cornea," *Journal of Biomechanics*, vol. 24, No. 10, Apr. 1991, pp. 907-922 (15 pages).
Pinsky PM, Datye DV, "Numerical Modeling of Radial, Astigmatic, and Hexagonal Keratotomy," *Refractive and Corneal Surgery*, vol. 8, No. 2, Mar.-Apr. 1992, pp. 164-172 (11 pages).

Pinsky PM, van der Heide D, Chernyak D, "Computational Modeling of Mechanical Anisotropy in the Cornea and Sclera," *Journal of Cataract & Refractive Surgery*, vol. 31, Jan. 2005, pp. 136-145 (10 pages).

Riley C, Chalmers RL, "Survey of Contact Lens-Wearing Habits and Attitudes Toward Methods of Refractive Correction: 2002 Versus 2004," *Optometry and Vision Science*, vol. 82, No. 6, Jun. 2005, pp. 555-561 (7 pages).

Rosenbloom A, "New Aged and Old Aged: Impact of the Baby Boomer," *Journal of the American Optometry Association*, vol. 74, No. 4, Apr. 2003, pp. 211-213 (5 pages).

Rutzen AR, Roberts CW, Driller J, Gomez D, Lucas BC, Lizzi FL, Coleman DJ., "Production of Corneal Lesions Using High-Intensity Focused Ultrasound," *Cornea*, vol. 9, No. 4, Oct. 1990, pp. 324-330 (8 pages).

Ryan TP, Pertaub R, Meyers SR, Dresher RP, Scharf R., "Experimental Results of a New System Using Microwaves for Vision Correction," *Proceedings of SPIE*, vol. 7181, Feb. 2009, pp. 718106.1 to 718106.17 (17 pages).

Seiler T, Matallana M, Bende T, "Laser Thermokeratoplasty by Means of a Pulsed Holmium:YAG Laser for Hyperopic Correction," *Refractive and Corneal Surgery*, vol. 6, No. 5, Sep.-Oct. 1990, pp. 335-339 (6 pages).

Seiler T, Matallana M, Sendler S, Bende T, "Does Bowman's Layer Determine the Biomechanical Properties of the Cornea?" *Refractive and Corneal Surgery*, vol. 8, No. 2, Mar.-Apr. 1992, pp. 139-142 (6 pages).

Shin TJ, Vito RP, Johnson LW, McCarey BE, "The Distribution of Strain in the Human Cornea," Journal of Biomechanics, vol. 30, No. 5, May 1997, pp. 497-503 (7 pages).

Solomon KD, Fernandez de Castro LE, Sandoval HP, Biber JM, Groat B, Neff KD, Ying MS, French JW, Donnenfeld ED, Lindstrom RL, "LASIK World Literature Review: Quality of Life and Patient Satisfaction," *Ophthalmology*, vol. 116, No. 4, Apr. 2009, pp. 691-701 (11 pages).

Stanley PF, Tanzer DJ, Schallhorn SC, "Laser Refractive Surgery in the United States Navy," *Current Opinion Ophthalmology*, vol. 19, Jul. 2008, pp. 321-324 (4 pages).

Strenk SA, Strenk LM, Koretz JF, "The Mechanism of Presbyopia," *Progress in Retinal Eye Research*, vol. 24, May 2005, pp. 379-393 (15 pages).

Stringer H, Parr J., "Shrinkage Temperature of Eye Collagen," *Nature*, Dec. 1964, p. 1307 (1 page).

Sutton G., Patmore A.L., Joussen A.M., Marshall J., "Mannose 6-Phosphate Reduces Haze Following Excimer Laser Photorefractive Keratectomry," *Lasers and Light*, vol. 7, No. 2/3, 1996, pp. 117-119 (3 pages).

Telandro A., "Pseudo-Accommodation Cornea: a New Concept for Correction of Presbyopia," *Journal of Refractive Surgery*, vol. 20, No. 5, Sep.-Oct. 2004, pp. S714-S717 (5 pages).

Trembly BS, Hashizume N, Moodie KL, Cohen KL, Tripoli NK, Hoopes PJ, "Microwave Thermal Keratoplasty for Myopia: Keratoscopic Evaluation in Porcine Eyes," *Journal of Refractive Surgery*, vol. 17, No. 6, Nov.-Dec. 2001, pp. 682-688 (8 pages).

Trembly BS, Keates RH, "Combined Microwave Heating and Surface Cooling of the Cornea," *IEEE Transactions on Biomedical Engineering*, vol. 38, No. 1, Jan. 1991, pp. 85-91 (8 pages).

Truscott RJ, "Presbyopia Emerging from a Blur Towards an Understanding of the Molecular Basis for this Most Common Eye Condition," *Experimental Eye Research*, vol. 88, Feb. 2009, pp. 241-247 (7 pages).

Uchio E, Ohno S, Kudoh J, Aoki K, Kisielewicz LT, "Simulation Model of an Eyeball Based on Finite Element Analysis on a Supercomputer," *British Journal of Ophthalmology*, vol. 83, Jun. 1999, pp. 1106-1111 (7 pages).

Wang JQ, Zeng YJ, Li XY, "Influence of Some Operational Variables on the Radial Keratotomy Operation," *British Journal of Ophthalmology*, vol. 84, Jan. 2000, pp. 651-6533 (4 pages).

Wollensak, G., et al., "Riboflavin/Ultraviolet-A-Induced Collagen Crosslinking for the Treatment of Keratoconus," *American Journal of Ophthalmology, Ophthalmic Publ.*, Chicago, IL, US, vol. 135, No. 5, May 1, 2003, pp. 620-627 (8 pages).

Zelichowska B, Rekas M, Stankiewicz A, Cervino A, Montés-MicóR., "Apodized Diffractive Versus Refractive Multifocal Intraocular Lenses: Optical and Visual Evaluation," *Journal of Cataract & Refractive Surgery*, vol. 34, Dec. 2008, pp. 2036-2042 (7 pages).

* cited by examiner

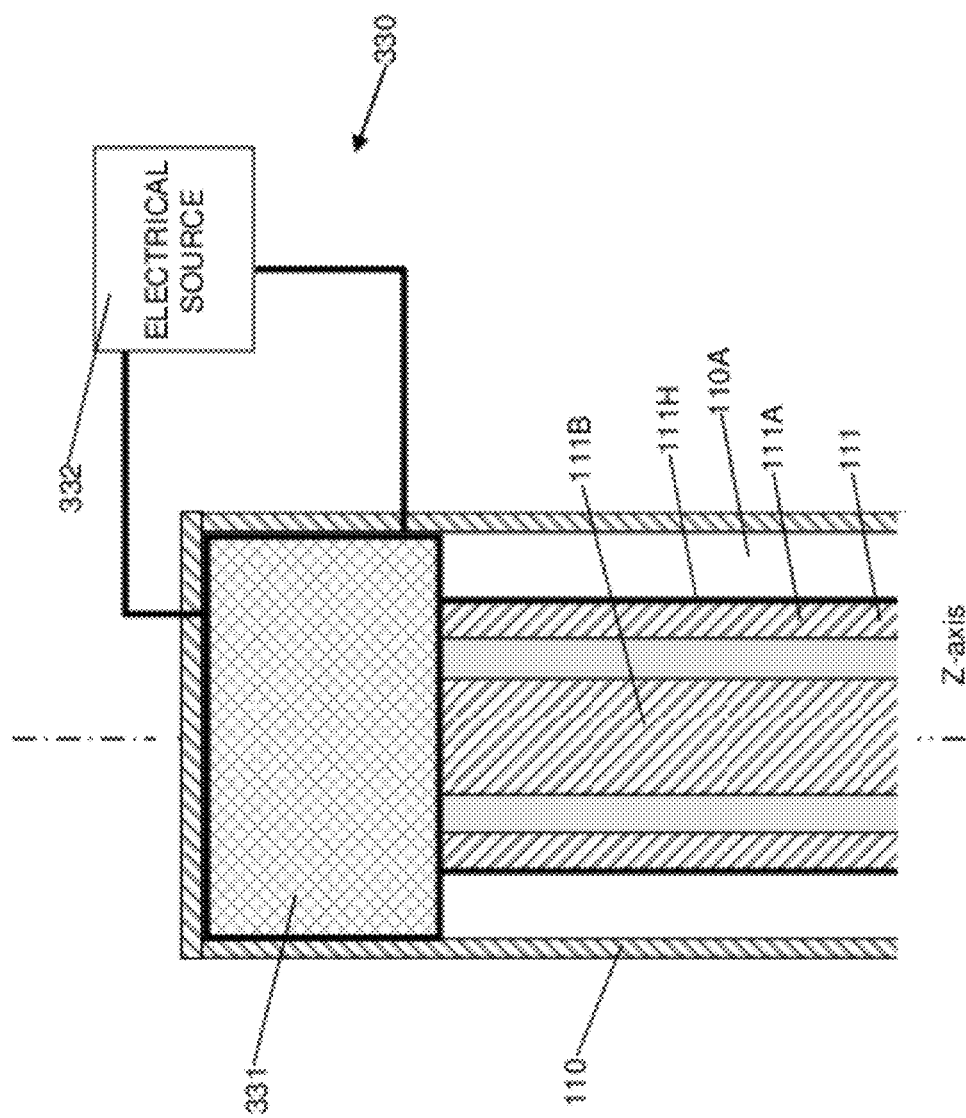

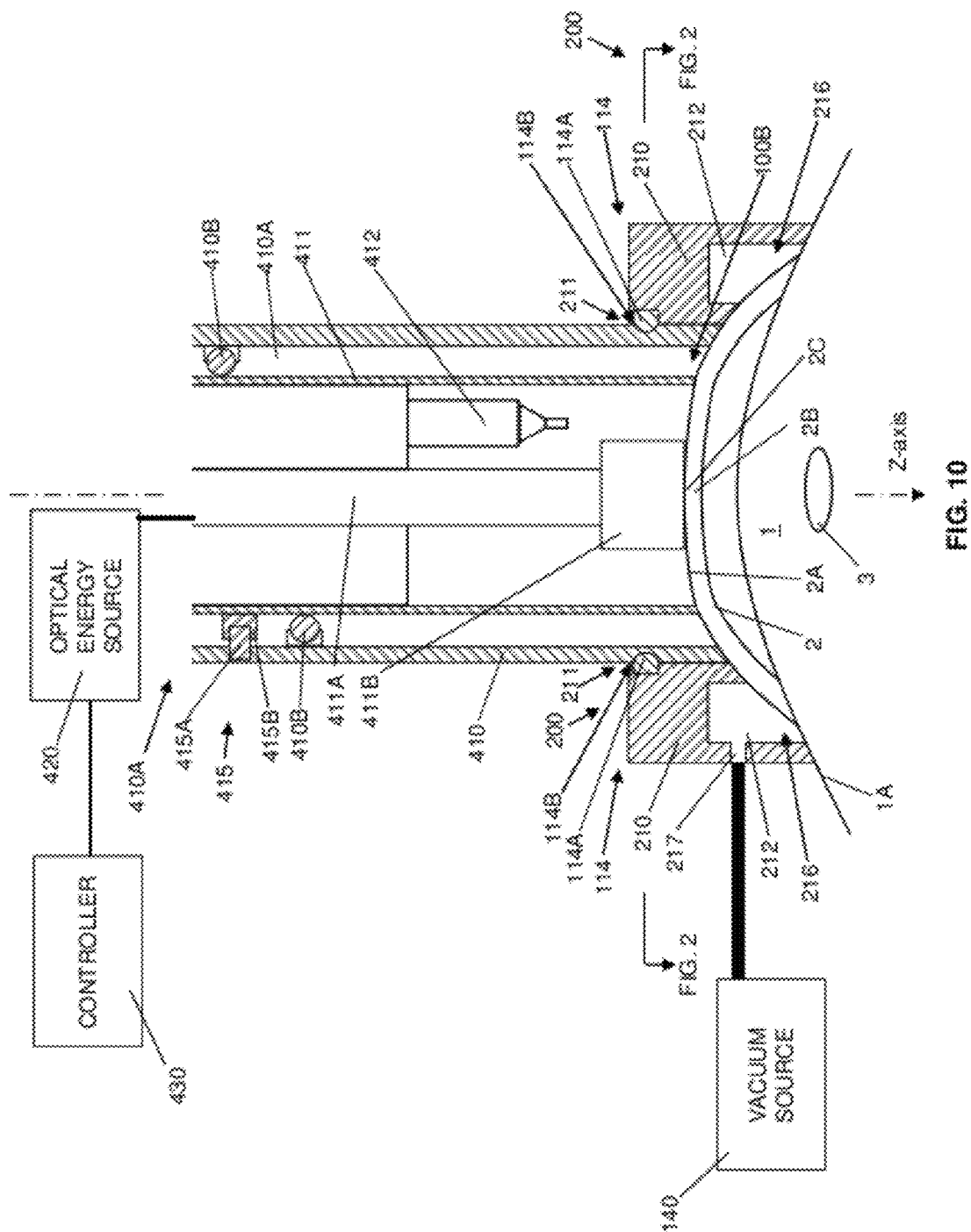

SYSTEM AND METHOD FOR RESHAPING AN EYE FEATURE

BACKGROUND OF THE INVENTION

1. Field of the Invention

The invention pertains generally to the field of keratoplasty and, more particularly, to a system and method for accurately and consistently applying a thermokeratoplasty applicator to the cornea.

2. Description of Related Art

A variety of eye disorders, such as myopia, keratoconus, and hyperopia, involve abnormal shaping of the cornea. Keratoplasty reshapes the cornea to correct such disorders. For example, with myopia, the shape of the cornea causes the refractive power of an eye to be too great and images to be focused in front of the retina. Flattening aspects of the cornea's shape through keratoplasty decreases the refractive power of an eye with myopia and causes the image to be properly focused at the retina.

Invasive surgical procedures, such as laser-assisted in-situ keratonomileusis (LASIK), may be employed to reshape the cornea. However, such surgical procedures typically require a healing period after surgery. Furthermore, such surgical procedures may involve complications, such as dry eye syndrome caused by the severing of corneal nerves.

Thermokeratoplasty, on the other hand, is a noninvasive procedure that may be used to correct the vision of persons who have disorders associated with abnormal shaping of the cornea, such as myopia, keratoconus, and hyperopia. Thermokeratoplasty, for example, may be performed by applying electrical energy in the microwave or radio frequency (RF) band. In particular, microwave thermokeratoplasty may employ a near field microwave applicator to apply energy to the cornea and raise the corneal temperature. At about 60° C., the collagen fibers in the cornea shrink. The onset of shrinkage is rapid, and stresses resulting from this shrinkage reshape the corneal surface. Thus, application of energy in circular, ring-shaped patterns around the pupil generates heat that may cause aspects of the cornea to flatten and improve vision in the eye. Although thermokeratoplasty has been identified as a technique for eye therapy, there is a need for a practical system that enables more accurate and precise application of thermokeratoplasty in a clinical setting.

SUMMARY OF THE INVENTION

In general, the pattern of energy applied to an eye feature during thermokeratoplasty depends on the position of the energy applicator relative to the eye feature, such as a cornea. Thus, to provide reliable application of energy to the eye feature, embodiments according to aspects of the present invention position the applicator in uniform and constant contact with the eye feature while the applicator provides eye therapy. In this way, the relationship between the applicator and the eye feature is more definite and the resulting delivery of energy is more predictable and accurate. The positioning of the applicator provides better electrical and thermal contact. Advantageously, these embodiments also provide a system and method for accurately reproducing sufficient contact between the applicator and the eye feature.

For example, an embodiment provides a system for applying therapy to an eye including an applicator having a conducting element configured to direct energy from an energy source to an application end of the conducting element, where the application end has an eye contact portion. The energy source in this embodiment may be an electrical energy source, and the conducting element may include an outer electrode and an inner electrode separated by a gap, where the two electrical conductors define the application end with the eye contact portion. A positioning system is configured to receive the applicator and position the eye contact portion in stable engagement with the surface of an eye during the application of energy to a targeted feature of the eye, such as the cornea.

In some embodiments, the conducting element is disposed within a housing for the applicator, and an adjustment system is employed to move the conducting element relative to the housing. With the positioning system being attached to the eye surface and the applicator housing being fixed relative to the positioning system, the adjustment system enables controlled movement of the conducting element and the eye contact portion against the eye surface to cause sufficient contact with the targeted eye feature. The adjustment system, for example, may be an electromechanical system.

In particular embodiments, sufficient contact between the applicator and the cornea is determined by causing an observable amount of flattening, or applanation, of the cornea. The applanation provides a constant and uniform pressure against the corneal surface. In other embodiments, a physical measurement device, such as a strain gauge, may be employed to determine when sufficient contact has been established. With such approaches, embodiments can consistently reproduce a specified amount of contact.

While some embodiments may move the applicator into contact against the cornea, further embodiments may employ a controlled vacuum source, for example, to draw or suction the cornea into sufficient contact against the applicator.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 8 illustrates a cross-sectional view of an embodiment that employs yet another electromechanical element to position an energy conducting element according to aspects of the present invention.

FIG. 10 illustrates a cross-sectional view of an embodiment employing a positioning system that receives and moves an optical energy conducting element into engagement with the cornea according to aspects of the present invention.

DETAILED DESCRIPTION

Figure 1:
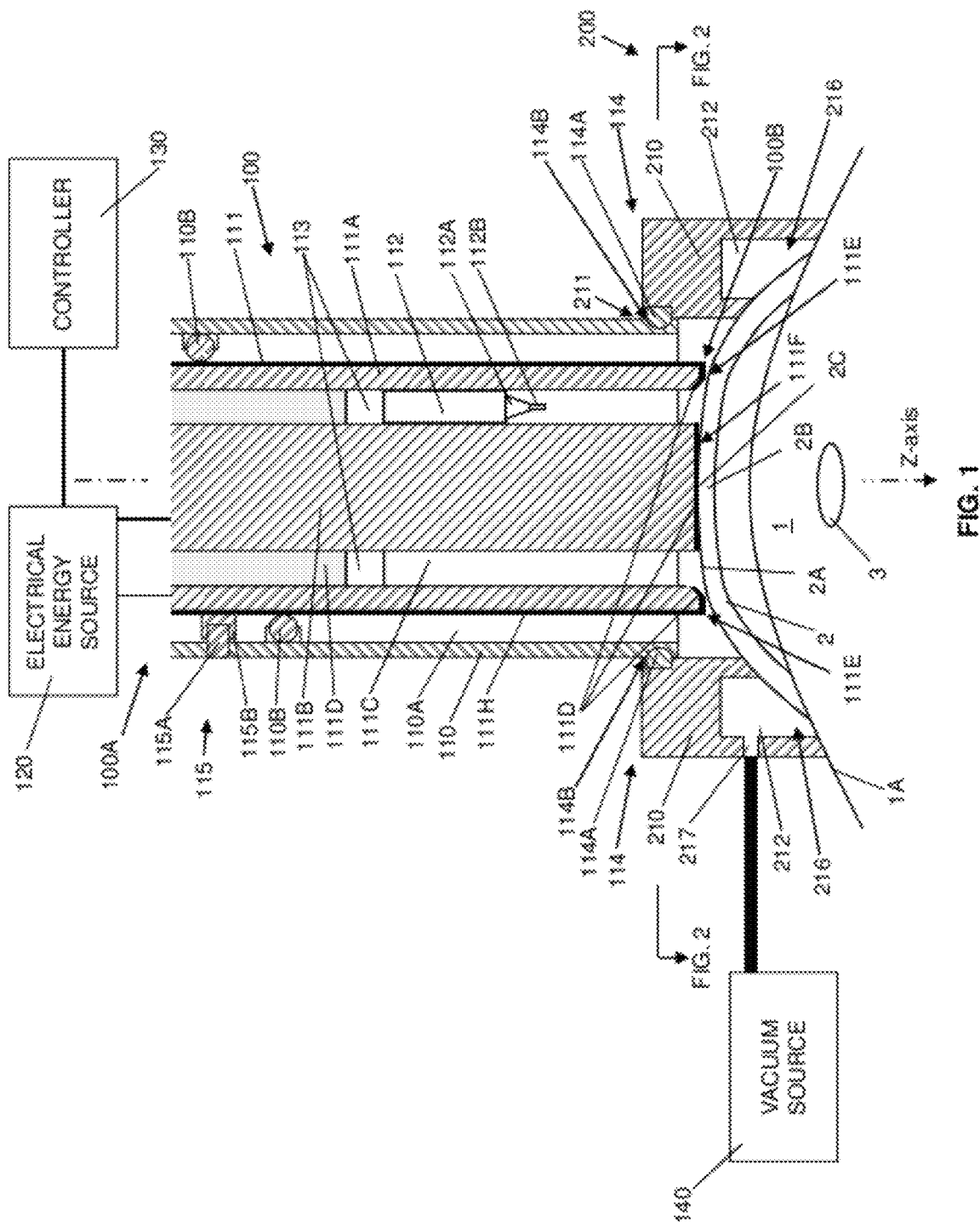
FIG. 1 illustrates a cross-sectional view of an embodiment employing a positioning system that receives and moves an electrical energy conducting element into engagement with the cornea according to aspects of the present invention.

Referring to the cross-sectional view of FIG. 1, a system for applying energy to a cornea 2 of an eye 1 to achieve corrective reshaping of the cornea is illustrated. In particular, FIG. 1 shows an applicator 100 that includes a housing 110 and an energy conducting element 111, which extend from a proximal end 100A to a distal end 100B. The energy conducting element 111 is positioned within a passageway 110A which extends longitudinally through the housing 110. Any number of bearings 110B, or similar guiding structures, may be employed to keep the energy conducting element 111 substantially centered within the passageway 110A. An electrical energy source 120 is operably connected to the energy conducting element 111 at the distal end 100B, for example, via conventional conducting cables. The electrical energy source 120 may include a microwave oscillator for generating microwave energy. For example, the oscillator may operate at a microwave frequency range of 500 MHz to 3000 MHz, and more specifically at a frequency of around 915 MHz which provides safe use of the energy conducting element 111. Although embodiments described herein may employ microwave frequencies, it is contemplated that any frequency, e.g., including microwave, radio-frequency (RF), etc., may be employed. For example, embodiments may employ radiation having, but not limited to, a frequency between 10 MHz and 300 GHz.

Operation of the energy source 120 causes energy to be conducted through the energy conducting element 111 to the distal end 100B. As such, the applicator 100 may be employed to apply energy to the cornea 2 of the eye 1 which is positioned at the distal end 100B. As shown further in FIG. 1, the distal end 100B is positioned over the cornea 2 by a positioning system 200. In general, the positioning system 200 provides support for the applicator 100 so that the energy conducting element 111 can be operated to deliver energy to targeted areas of the cornea 2. The positioning system 200 includes an attachment element 210 which receives the applicator housing 110. Meanwhile, the attachment element 210 can be fixed to a portion of the eye surface 1A, such as the area surrounding the portion of the cornea 2 being treated. The attachment element 210 situates the applicator 100 in a stable position for delivering energy to the cornea 2.

Figure 2:
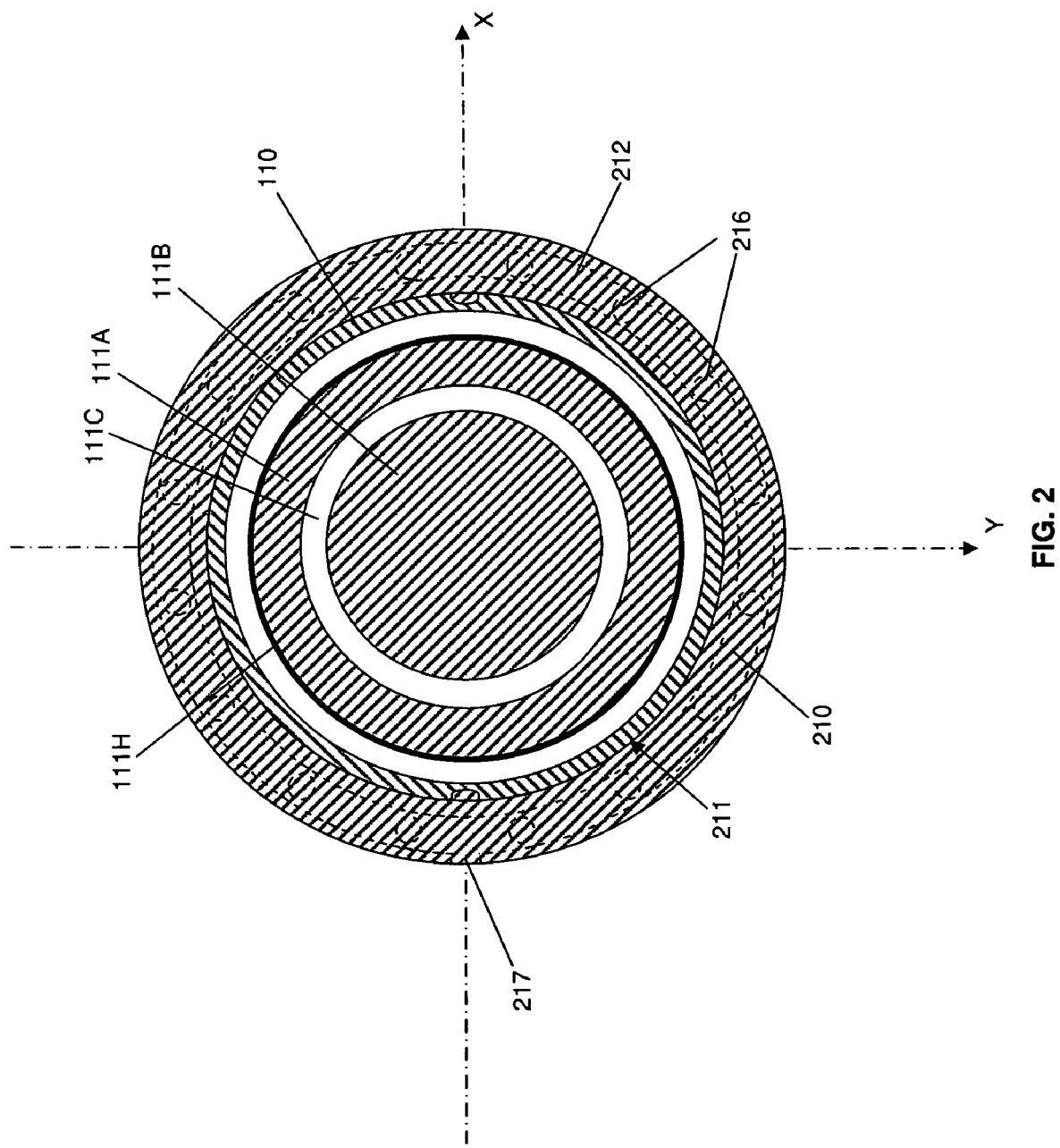
FIG. 2 illustrates another cross-sectional view of the embodiment of FIG. 1.

As shown in FIG. 1, the attachment element 210 of the positioning system 200 may have a substantially annular structure defining a central passageway 211 through which the applicator housing 110 can be received and the cornea 2 can be accessed. In some embodiments, for example, an outer diameter of the annular structure may range from approximately 18 mm to 23 mm while an inner diameter may range from approximately 11 mm to 15 mm to accommodate aspects of the eye 1 and the cornea 2. The attachment element 210 may be attached to portions of the eye surface 1A by creating a vacuum connection with the eye surface 1A. As such, the attachment element 210 of FIG. 1 acts as a vacuum ring that includes an interior channel 212 which is operably connected to a vacuum source 140 via connection port 217. The attachment element 210 also includes a plurality of openings 216 which open the interior channel 212 to the eye surface 1A. The attachment element 210 may be formed from a biocompatible material such as a titanium alloy or the like. FIG. 2 illustrates a cross-sectional view of the attachment element 210, including the central passageway 211, the interior channel 212, the plurality of openings 216, and the connection port 217. FIG. 2 also shows the housing 110 being received within the central passageway 211.

When the openings 216 are positioned in contact with the eye surface 1A and the vacuum source 140 is activated to create a near vacuum or low pressure within the interior channel 212, the openings 216 operate to suction the attachment element 210 and the eye surface 1A together. To promote sufficient suction between the eye surface 1A and the attachment element 210, the bottom surface 213 of the attachment element 210 may be contoured to fit the shape of the eye more closely. In one example, the vacuum source 140 may be a syringe, but the vacuum source 140 may be any manual or automated system that creates the appropriate amount of suction between the attachment element 210 and the eye surface 1A. Although the attachment element 210 can be stably attached to the eye surface 1A, the attachment element 210 can be detached by removing the vacuum source 140 and equalizing the pressure in the interior channel 212 with the exterior environment.

When applying energy to the cornea 2, the applicator 100 may be centered, for example, over the pupil 3, which is generally coincident with a center portion 2C of the cornea 2. In some embodiments, the positioning system 200 may provide an additional receiving element that is coupled to the attachment element 210 and movable relative to the attachment element 210. The receiving element receives the energy conducting element 111 and can be moved to adjust the position of the energy conducting element 111 with respect to the attachment element 210 and the cornea 2. As such, the energy conducting element 111 can be accurately positioned over the cornea 2 via the position system. In general, the positioning system 200 enables the energy conducting element 111 to apply energy to desired areas of the cornea 2, for example centered about the pupil 3, to achieve the desired reshaping of the cornea 2.

Once the applicator 100 is positioned by the positioning system 200, the energy conducting element 111 can deliver energy to targeted areas of collagen fibers in a mid-depth region 2B of the cornea 2 to shrink the collagen fibers according to a predetermined pattern and reshape the cornea 2 in a desired manner, thereby improving vision through the eye 1. For example, a contribution to the corneal reshaping comes from the contraction of the collagen fibrils found in the upper third of the corneal stroma, lying approximately 75-150 microns below the corneal, i.e., epithelial, surface 2A.

As further illustrated in FIG. 1, the electrical energy conducting element 111 includes two microwave conductors 111A and 111B, which extend from the proximal end 100A to the distal end 100B of the applicator 100. For example, as also illustrated in FIG. 2, the conductor 111A may be a substantially cylindrical outer conductor, while the conductor 111B may be a substantially cylindrical inner conductor that extends through an inner passage extending through the outer conductor 111A. With the inner passage, the outer conductor 111A has a substantially tubular shape. The inner and the outer conductors 111A and 111B may be formed, for example, of aluminum, stainless steel, brass, copper, other metals, metal-coated plastic, or any other suitable conductive material. At the distal end 100B of the applicator 100, the outer conductor 111A has a distal surface 111E and the inner conductor 111B has a distal surface 111F. As described in further detail below, the distal surfaces 111E and 111F, or portions thereof, provide an eye contact portion that can be applied against the cornea 2, as shown in FIG. 1. Although the distal surfaces 111E and 111B in FIG. 1 appear to be located at substantially the same position along the Z-axis, it is contemplated that the distal surface 111E of the outer electrode 111A may extend past the distal surface 111F of the inner electrode 111B, or alternatively, the position of the distal surface 111F may be in a recessed position with respect to the distal surface 111E.

With the concentric arrangement of conductors 111A and 111B shown in FIG. 2, a substantially annular gap 111C of a selected distance is defined between the conductors 111A and 111B. The annular gap 111C extends from the proximal end 100A to the distal end 100B. A dielectric material 111D may be used in portions of the annular gap 111C to separate the conductors 111A and 111B. The distance of the annular gap 111C between conductors 111A and 111B determines the penetration depth of microwave energy into the cornea 2 according to established microwave field theory. Thus, the microwave conducting element 111 receives, at the proximal end 100A, the electrical energy generated by the electrical energy source 120, and directs microwave energy to the distal end 111B, where the cornea 2 is positioned in accordance with the positioning system 200.

The outer diameter of the inner conductor 111B is preferably larger than the pupil 3, over which the applicator 100 is centered. In general, the outer diameter of the inner conductor 111B may be selected to achieve an appropriate change in corneal shape, i.e. keratometry, induced by the exposure to microwave energy. The outer diameter of the inner electrode 111B determines the diameter across which the refractive change to the cornea 2 is made. When the energy conducting element is applied to the corneal surface 2A, the area of the cornea 2 at the periphery of the inner electrode 111B is subject to an energy pattern with substantially the same shape and dimension as the gap 111C between the two microwave conductors 111A and 111B.

Meanwhile, the inner diameter of the outer conductor 111A may be selected to achieve a desired gap between the conductors 111A and 111B. For example, the outer diameter of the inner conductor 111B ranges from about 4 mm to about 10 mm while the inner diameter of the outer conductor 111A ranges from about 4.1 mm to about 12 mm. In some systems, the annular gap 111C may be sufficiently small, e.g., in a range of about 0.1 mm to about 2.0 mm, to minimize exposure of the endothelial layer of the cornea (posterior surface) to elevated temperatures during the application of energy by the applicator 100.

A controller 130 may be employed to selectively apply the energy any number of times according to any predetermined or calculated sequence. In addition, the energy may be applied for any length of time. Furthermore, the magnitude of energy being applied may also be varied. Adjusting such parameters for the application of energy determines the extent of changes that are brought about within the cornea 2. Of course, the system attempts to limit the changes in the cornea 2 to an appropriate amount of shrinkage of collagen fibrils in a selected region. When applying microwave energy to the cornea 2 with the applicator 100, the microwave energy may be applied with low power (of the order of 40 W) and in long pulse lengths (of the order of one second). However, other systems may apply the microwave energy in short pulses. In particular, it may be advantageous to apply the microwave energy with durations that are shorter than the thermal diffusion time in the cornea. For example, the microwave energy may be applied in pulses having a higher power in the range of 500 W to 3 KW and a pulse duration in the range of about 10 milliseconds to about one second.

Referring again to FIG. 1, at least a portion of each of the conductors 111A and 111B may be covered with an electrical insulator to minimize the concentration of electrical current in the area of contact between the corneal surface (epithelium) 2A and the conductors 111A and 111B. In some systems, the conductors 111A and 111B, or at least a portion thereof, may be coated with a material that can function both as an electrical insulator as well as a thermal conductor. A dielectric material 111D may be employed along the distal end 100B of the applicator 100 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibrils in a mid-depth region 2B of the cornea 2. Accordingly, the dielectric material 111D is positioned between the conductors 111A and 111B and the cornea 2. In particular, as shown in FIG. 1, the distal surfaces 111E and 111F of the conductors 111A and 111B include a dielectric material 111D. The dielectric material 111D may be sufficiently thin to minimize interference with microwave emissions and thick enough to prevent superficial deposition of electrical energy by flow of conduction current. For example, the dielectric material 111D may be a biocompatible material, such as Teflon®, deposited to a thickness of about 0.002 inches. In general, an interposing layer, such as the dielectric material 111D, may be employed between the conductors 111A and 111B and the cornea 2 as long as the interposing layer does not substantially interfere with the strength and penetration of the microwave radiation field in the cornea 2 and does not prevent sufficient penetration of the microwave field and generation of a desired energy pattern in the cornea 2. Of course, the dielectric material 111D may be omitted and electrical energy in the microwave or radio frequency (RF) band may be applied directly. A similar electrically insulating material 111H may also be employed on the outer surface of the outer electrode 111A.

During operation, the distal end 100B of the applicator 100 as shown in FIG. 1 is positioned by the positioning system 200 at the corneal surface 2A. The applicator 100 positions the energy conducting element 111 to make direct contact with the corneal surface 2A. As such, the distal surfaces 111E and 111F of the conductors 111A and 111B, respectively, are positioned against the corneal surface 2A. The positioning of the conductors 111A and 111B helps ensure that the pattern of microwave energy in the corneal tissue has substantially the same shape and dimension as the gap 111C between the two microwave conductors 111A and 111B.

As shown in FIG. 1, the applicator 100 may also employ a coolant system 112 that selectively applies coolant to the corneal surface 2A to minimize heat-related damage to the corneal surface 2A during thermokeratoplasty and to determine the depth of energy delivered below the corneal surface 2A to the mid-depth region 2B. Such a coolant system enables the energy conducting element 111 to be placed into direct contact with the corneal surface 2A without causing heat-related damage. In some embodiments, the coolant may also be applied after the application of energy to preserve, or "set," the desired shape changes by eliminating further presence of energy and preventing further changes to the new corneal shape. Examples of such a coolant system are described in U.S. application Ser. No. 11/898,189, filed Sep. 10, 2007, the contents of which are entirely incorporated herein by reference. For example, the coolant delivery system 112 as well as a coolant supply 113 may be positioned within the annular gap 111C. Although FIG. 1 may illustrate one coolant delivery system 112, the applicator 100 may include a plurality of coolant delivery systems 112 arranged circumferentially within the annular gap 111C. The coolant supply 113 may be an annular container that fits within the annular gap 111C, with the coolant delivery element 112 having a nozzle structure 112A extending downwardly from the coolant supply 113 and an opening 112B directed toward the distal end 100B. The coolant may be a liquid cryogen, such as tetrafluoroethane. Alternatively, the coolant may be a cool gas, such as nitrogen gas, e.g., blowoff from a liquid nitrogen source.

In some embodiments, the coolant system 112 is operated, for example, with the controller 130 to deliver pulses of coolant in combination with the delivery of energy to the cornea 2. Advantageously, applying the coolant in the form of pulses can help prevent the creation of a fluid layer between the conductors 111A and 111B and the corneal surface 2A that interferes with the delivery of energy from the energy conducting electrode 111. In particular, the short pulses of coolant may evaporate from the corneal surface 2A or may be removed, for example, by a vacuum (not shown) before the application of the microwave energy. Rather than creating an annular energy pattern according to the dimensions of the conductors 111A and 111B, the presence of a fluid layer may disadvantageously cause a less desirable circle-shaped microwave energy pattern in the cornea 2 with a diameter less than that of the inner conductor 111B. Therefore, to achieve a desired microwave pattern in some embodiments, a substantial flow of coolant or a cooling layer does not exist over the corneal surface 2A during the application of energy to the cornea 2. To further minimize the presence of a fluid layer, as described previously, the coolant may actually be a cool gas, rather than a liquid coolant.

Additionally or alternatively, heat sinks may also be employed to direct heat away from the corneal surface 2A and reduce the temperature at the surface 2A.

Figure 3A:
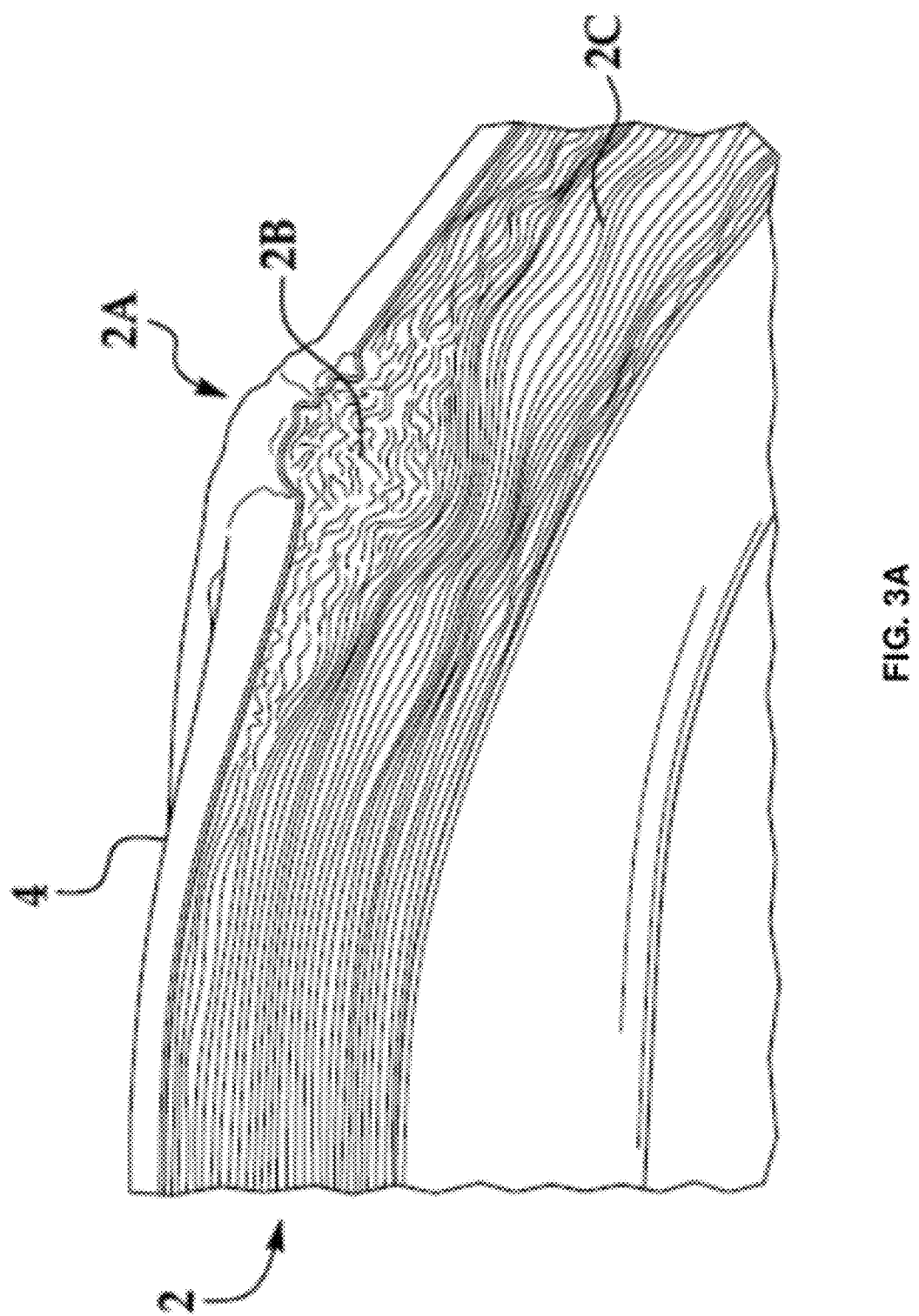
FIG. 3A illustrates an image of a cornea after energy has been applied.
Figure 3B:
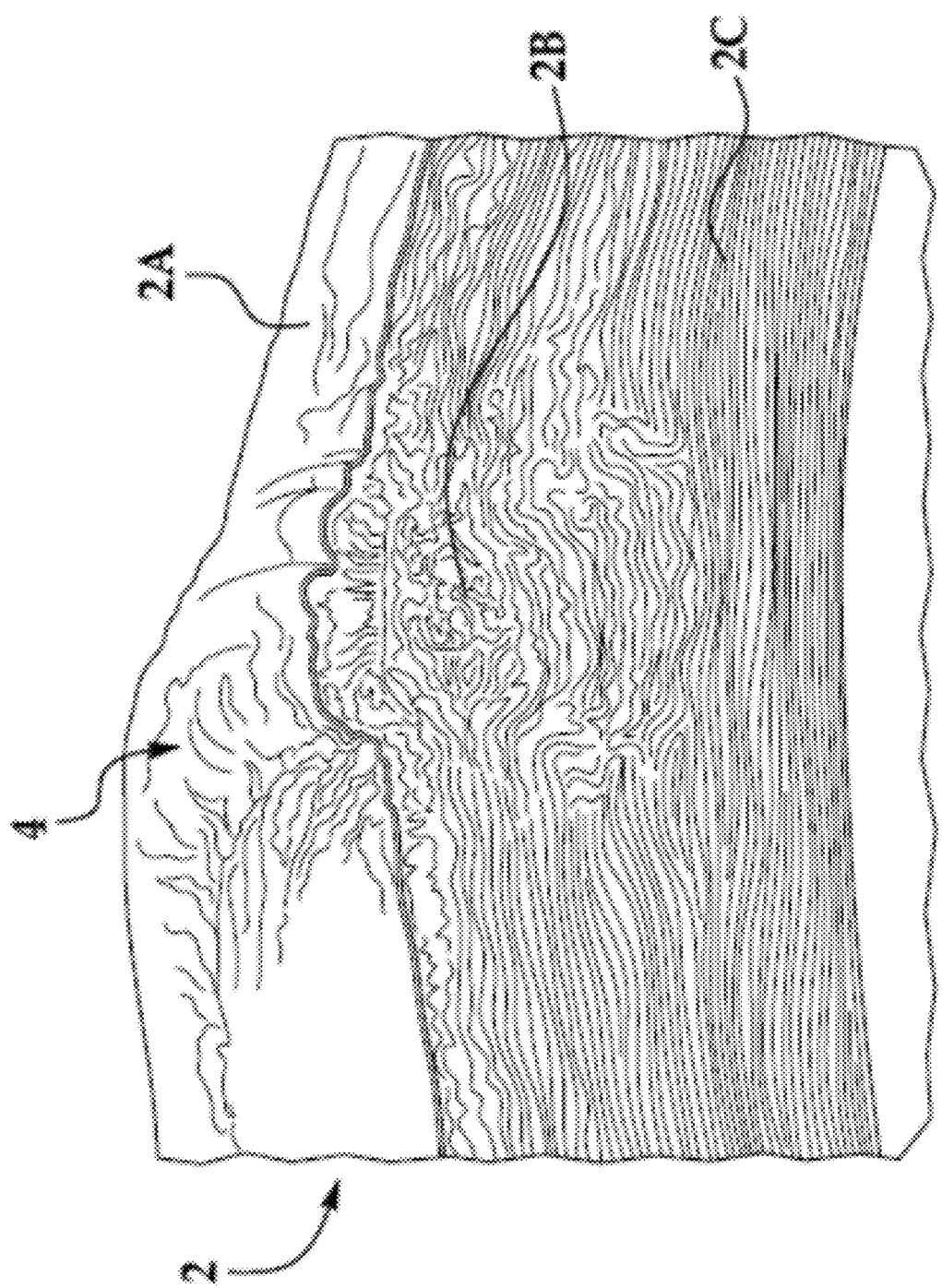
FIG. 3B illustrates another image of the cornea of FIG. 3A.

FIGS. 3A-D illustrate an example of the effect of applying energy to corneal tissue with a system for applying energy, such as the system illustrated in FIG. 1. In particular, FIGS. 3A and 3B illustrate high resolution images of the cornea 2 after energy has been applied. As FIGS. 3A and 3B show, a lesion 4 extends from the corneal surface 3A to a mid-depth region 3B in the corneal stroma 2D. The lesion 4 is the result of changes in corneal structure induced by the application of energy as described above. These changes in structure result in an overall reshaping of the cornea 2. It is noted that the application of energy, however, has not resulted in any heat-related damage to the corneal tissue.

Figure 3C:
FIG. 3C illustrates an image of the cornea of FIG. 3A.
Figure 3D:
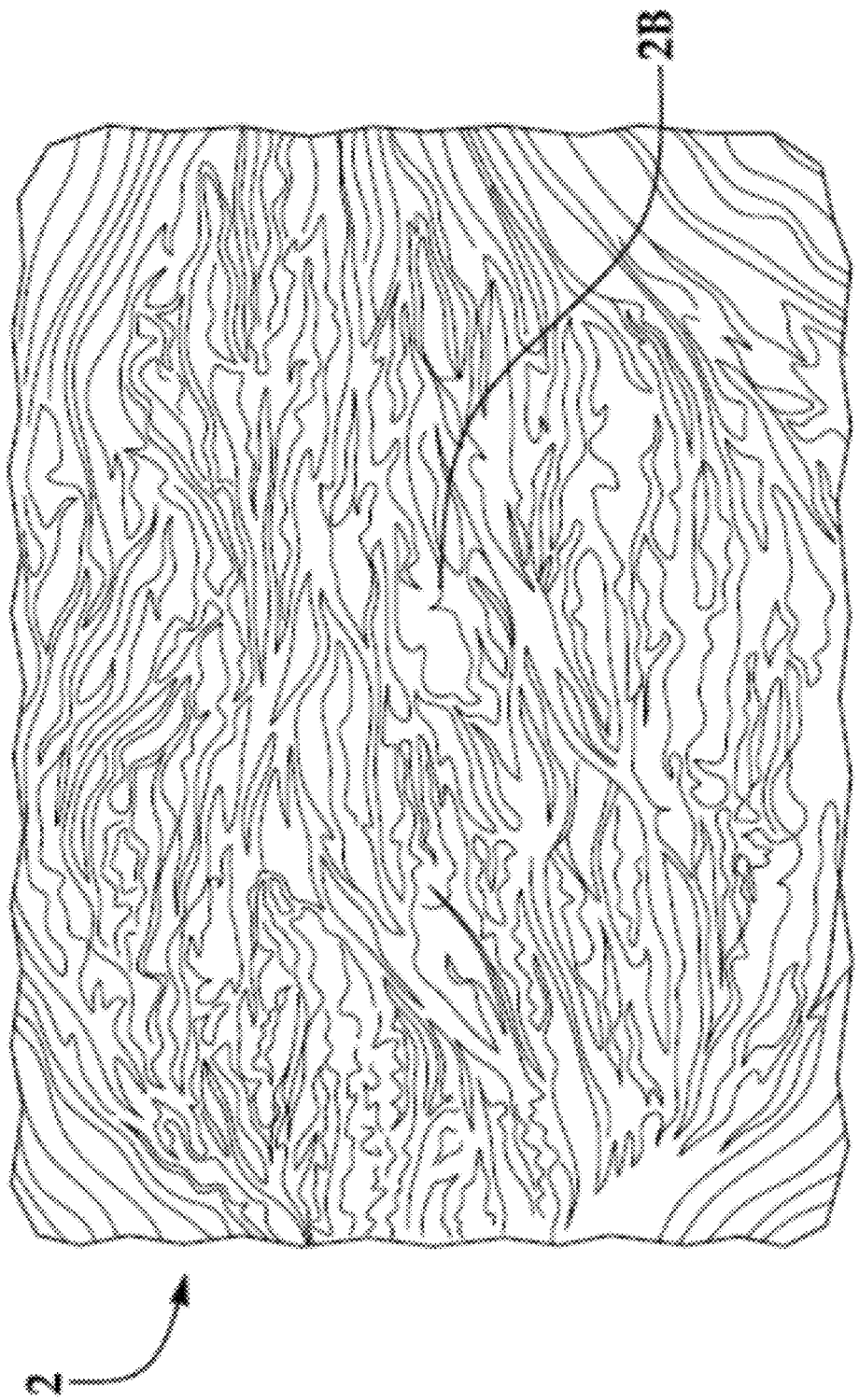
FIG. 3D illustrates another image of the cornea of FIG. 3A.

As further illustrated in FIGS. 3A and 3B, the changes in corneal structure are localized and limited to an area and a depth specifically determined by an applicator as described above. FIGS. 3C and 3D illustrate histology images in which the tissue shown in FIGS. 3A and 3B has been stained to highlight the structural changes induced by the energy. In particular, the difference between the structure of collagen fibrils in the mid-depth region 2B where energy has penetrated and the structure of collagen fibrils outside the region 2B is clearly visible. Thus, the collagen fibrils outside the region 2B remain generally unaffected by the application of energy, while the collagen fibrils inside the region 2B have been rearranged and form new bonds to create completely different structures. In sum, the corneal areas experience a thermal transition to achieve a new state.

The embodiments described herein provide a system and method by which the application of energy can accurately and precisely provide the changes in corneal shape that provide the desired improvements in the eye. Unlike other approaches, the embodiments provide consistent and reproducible results, especially to enable the eye therapy to be used in a clinical setting. As described previously, the energy pattern applied by the energy conducting element 111 may be affected by an intermediate fluid layer that interferes with the contact between the energy conducting element 111 and the corneal surface 2A. In general, the application of energy to the cornea 2 depends in part on the position of the distal surfaces 111E and 111F relative to the corneal surface 2A. As a result, to provide reliable application of energy to the cornea 2, embodiments ensure that the distal surfaces 111E and 111F are positioned to make contact with the corneal surface 2A. In this way, the relationship between the energy conducting element 411 and the cornea 2 is more definite and the resulting delivery of energy is more predictable and accurate.

In some embodiments, sufficient contact is determined by causing an observable amount of flattening, or applanation, of the cornea. The applanation provides a constant and uniform pressure against the corneal surface 2A. For example, as illustrated in FIG. 1, the applicator 100 can position the energy conducting element 111 against the corneal surface 2A so that the distal surface 111E of the outer electrode 111A and the distal surface 111F of the inner electrode 111B flattens the cornea 2. Although the distal surfaces 111E and 111F, or portions thereof, in contact with the corneal surface 2A are substantially flat, it is understood that the surfaces 111E and 111F may be shaped, e.g. contoured, in other ways to cause the desired contact. As shown in FIG. 1, the inner edge of the distal surface 111E of the outer electrode 111A may be beveled, or otherwise shaped, to minimize any pinching of the cornea 2 that may occur between the outer electrode 111A and the inner electrode 111B when the distal surfaces 111E and 111F are applied against the cornea 2. The applanation described herein adds precision and accuracy to the eye therapy procedure, particularly by improving electrical and thermal contact between the distal surfaces 111E and 111F and the corneal surface 2A.

The housing 110 and the positioning system 200 combine to keep the distal surfaces 111E and 111F in contact with the corneal surface 2A and maintain the applanation of the cornea 2 as energy is delivered via the energy conducting element 111. In addition, the housing 110 and the positioning system 200 combine to enable reproducible and predictable contact between the distal surfaces 111E and 111F and the corneal surface 2A. For example, as shown in FIG. 1, a first coupling system 114 may be employed to couple the housing 110 to the attachment element 210 of the positioning system 200. Once the housing 110 is guided fully into the attachment 210, the first coupling system 114 prevents the housing 110 from moving relative to the attachment element 210 along the Z-axis shown in FIG. 1.

As shown further in FIG. 1, the first coupling system 114 may include connecting elements 114A, which extend transversely from the attachment element 210 into cavities 114B in the applicator housing 110. As such, the applicator 110 is guided into the passageway 211 until the cavities 114B reach and engage the connecting elements 114A. In this way, the applicator 100 homes to a position determined by the connecting elements 114A, which act as stops. As such, the applicator 110 can be received into the same position relative to the attachment element 210 each time. The connecting elements 114A may be retractable to facilitate removal of the housing 110 from the attachment element 210. For instance, the connecting elements 114A may be rounded structures that extend from the housing 110 on springs (not shown).

It is understood, however, that the first coupling system 114 may employ other techniques, e.g. mechanically interlocking or engaging structures, for coupling the housing 110 to the attachment element 210. For example, the central passageway 211 of the attachment element 210 may have a threaded wall which receives the housing 110 in threaded engagement. In such an embodiment, the housing 110 may be screwed into the attachment element 210. The applicator can then be rotated about the Z-axis and moved laterally along the Z-axis to a desired position relative to the cornea 2. Stops may be included on the attachment element 210 to determine the target position of the applicator 100 in the passageway 211.

While the attachment element 210 keeps the applicator housing 110 in stable position relative to the cornea 2, the housing 110 in turn ensures that the distal surfaces 111E and 111F of the energy conducting element 111 maintain the desired amount of pressure against the cornea 2. For example, as shown in FIG. 1, a second adjustable coupling system 115 may be employed to couple the energy conducting element 110 to the housing 110. With the energy conducting element 111 positioned in the passageway 110A, the second coupling system 115 prevents the energy conducting element 111 from moving relative to the housing 110 along the Z-axis. For example, as illustrated in FIG. 1, the second coupling system 115 may include a connecting element 115A, such as a pin-like structure, which is positioned along the housing 110 and extends inwardly from the housing 110 into a cavity of a receiving structure 115B on the energy conducting element 111. Like the first coupling system 114, the second coupling system 115, of course, may employ other techniques for coupling the energy conducting element 111 to the housing 110. For example, in other embodiments, the energy conducting element 111 may be simply fastened or bonded to the inner walls of the housing 110 according to conventional methods. In general, the electrical conducting element 111, the housing 110, and the attachment element 210 are all fixed relative to each other while the attachment element 210 is attached to the corneal surface 2A. Accordingly, the energy conducting element 111 is able to apply constant pressure against the corneal surface 2A and flatten the cornea 2. The coupling systems 114 and 115 reproducibly determines the position of the energy conducting element 111 with respect to the cornea 2.

Figure 4:
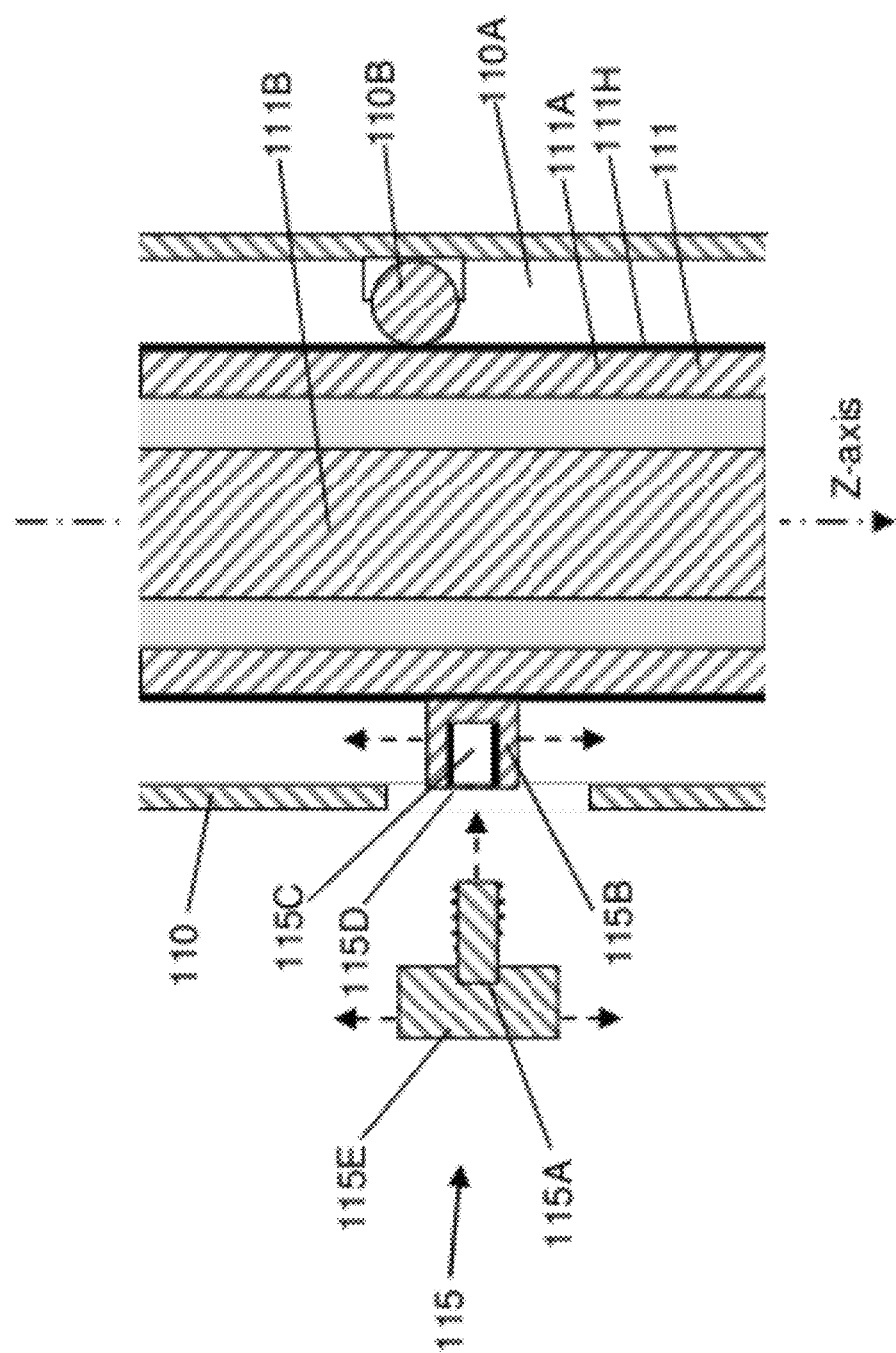
FIG. 4 illustrates an example of a coupling system for adjustably coupling an energy conducting element to an applicator housing according to aspects of the present embodiment.

The positions of the connecting element 115A and/or the receiving structure 115B may be adjustable to enable the energy conducting element 111 to occupy a selected position within the housing 110 and provide a desired amount of applanation. For example, as shown in FIG. 4, the connecting element 115A may be a threaded pin that is screwed into a corresponding threaded cavity 115C in the receiving structure 115B. Once the connecting element 115A is fully screwed into the cavity 115C, a head 115E of the connecting element 115A and the receiving structure 115B are held against the housing 110 by sufficient contact and friction to prevent movement of the connecting element 111A and the energy conducting element 111 along the Z-axis. The connecting element 115A can be positioned at various points in a slot, or opening, 115D that extends along the Z-axis in the housing 110. Therefore, the energy conducting element 111 can be moved to different positions along the Z-axis relative to the housing 110, and the connecting element 115A can be correspondingly moved in the slot 115 to be screwed into the receiving element 115B and couple the energy conducting element 111 to the housing 110. With the housing 110 fixed to the attachment element 210 on the corneal surface 2A, the ability to change the position of the energy conducting element 111 relative to the housing 110 means that the position of the distal ends 111E and 111F of the energy conducting element 111 relative to the corneal surface 2A can be changed. As a result, the amount of pressure on the cornea 2 can be adjusted to provide a particular amount of applanation. As long as the connecting element 115A remains in the same position relative to the housing 110, the particular amount of applanation is reproducible.

Figure 5:
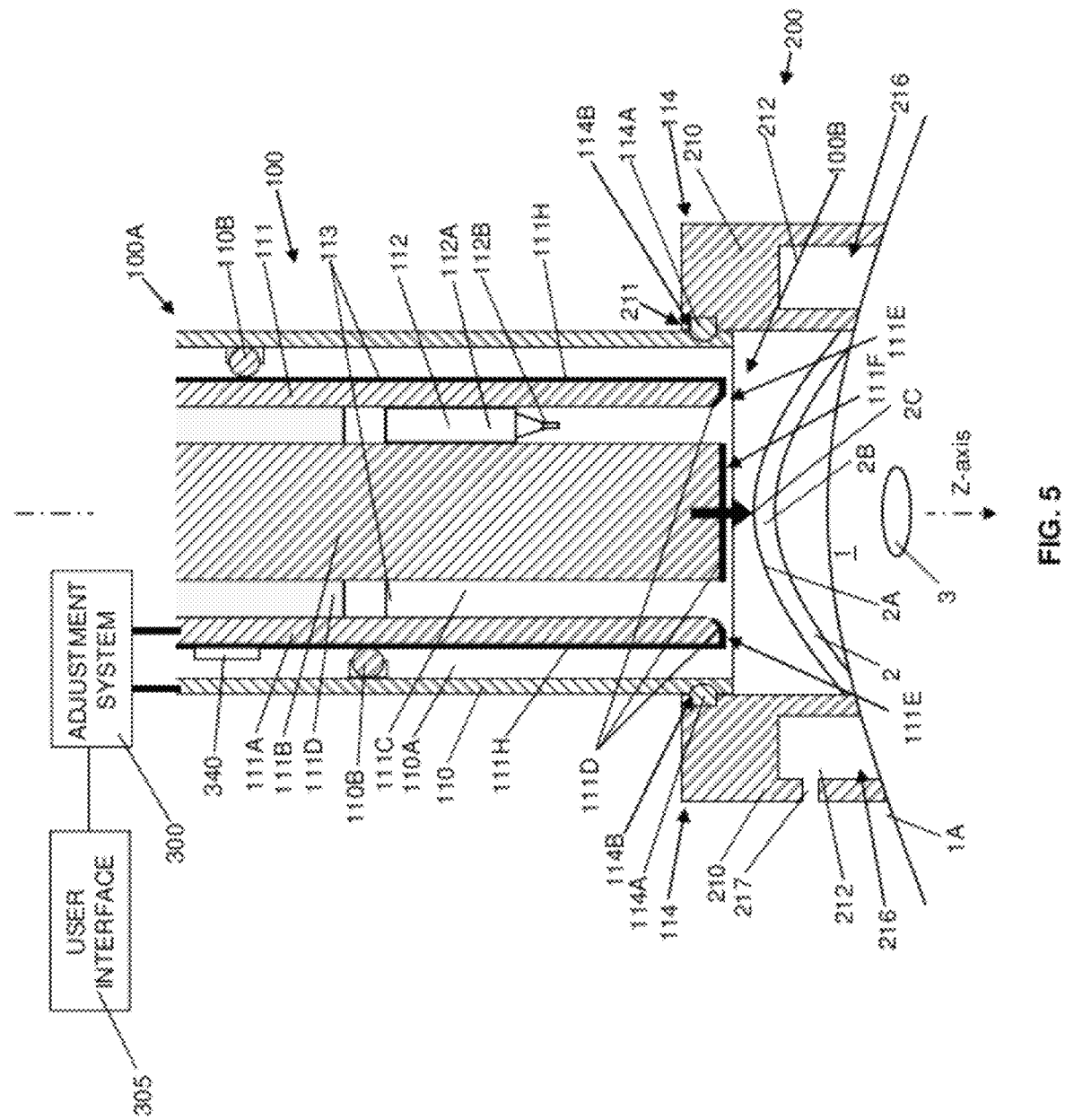
FIG. 5 illustrates an automated adjustment system for adjustably coupling an energy conducting element to an applicator housing according to aspects of the present embodiment.

FIG. 5 illustrates the movement of the energy conducting element 111 toward the cornea 2 within the housing 110 which is fixed relative to the cornea 2 with the attachment element 210. Although adjusting the position of the energy conducting element 111 relative to the housing 110 may be achieved manually, a more automated adjustment system 300, as shown in FIG. 5, can be employed to adjustably couple the energy conducting element 111 to the housing 110. Advantageously, the adjustment system 300 facilitates the accurate positioning of the energy conducting element 300 against the corneal surface 2A. After the attachment element 210 is fixed to the eye surface 1A, the applicator 100 is guided into position within the passageway 211 of the attachment element 210, and the adjustment system 300 can be easily operated to move the distal surfaces 111E and 111F of the energy conducting element 111 against the corneal surface 2A.

The adjustment system 300 may be further connected to a user interface system 305 that accepts input from a user and correspondingly operates the adjustment system 300. The user interface system 305, for example, may be a device with a keypad to receive input from a user. The keypad may be part of a processing system, such as a conventional personal computer, with software to control the adjustment system 300. Alternatively, the user interface system 305 may be a device, such as a joystick, that receives instructions from the user through more mechanically oriented input.

FIG. 5 illustrates the downward movement of the energy conducting device 111 relative to the housing 110 and the positioning system 200 and into contact with the corneal surface 2A. One or more stops may be employed to determine the extent of the downward movement of the energy conducting element 111 against the cornea 2. As described previously, the energy conducting device 111 may applied to cause applanation of the cornea 2, similar to the applanation shown in FIG. 1. The applanation indicates that sufficient contact has been established between the energy conducting device 111, i.e., the distal contact surfaces 111E and 111F, and the corneal surface 2A.

On the other hand, as shown further in FIG. 5, a physical measurement device 340 may be employed with the adjustment system 300 to measure the amount of pressure being applied by the distal surfaces 111E and 111F against the cornea 2. For example, the physical measurement device 340 may be a strain gauge that is able to detect the deformation in the energy conducting element 111 caused by contact with the corneal surface 2A. Therefore, the physical measurement device 340 indicates when the energy conducting element 111 has made sufficient contact with the corneal surface 2A and is applying constant and uniform pressure. As a result, applanation is not necessary to receive an indication that sufficient contact has been established with the cornea 2. The physical measurement device 340 also enables the application of a certain pressure to be reliably and accurately reproduced.

Figure 6:
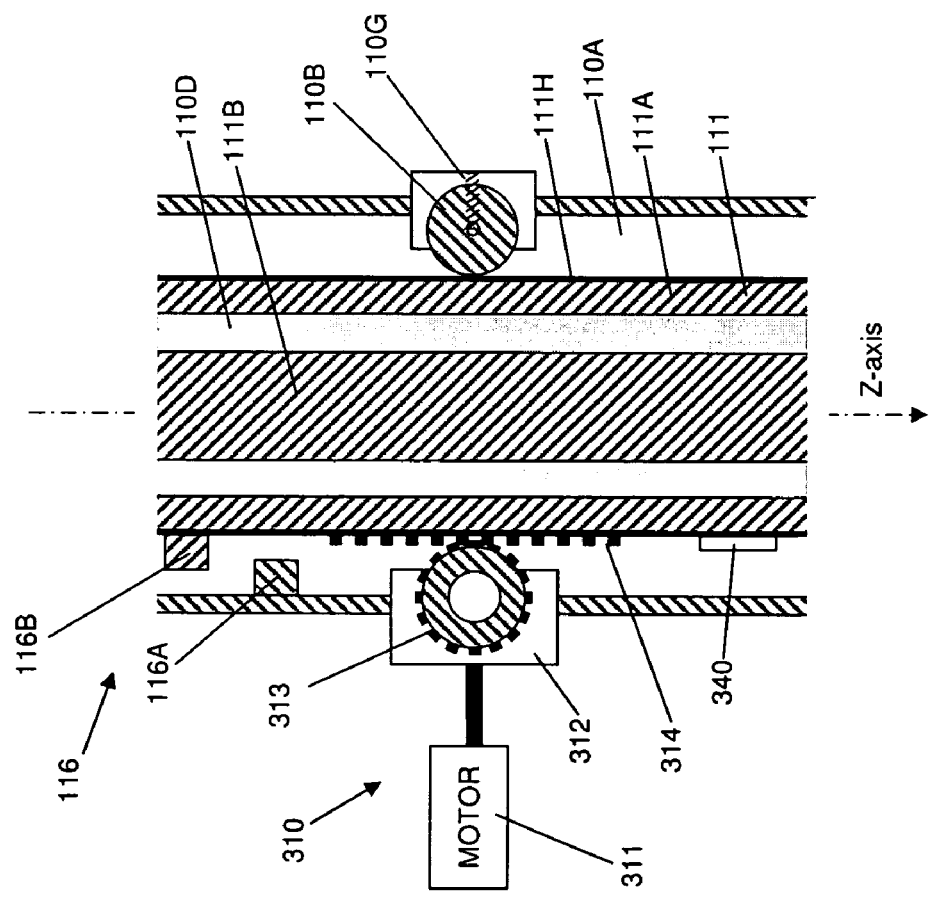
FIG. 6 illustrates a cross-sectional view of an embodiment that employs an electromechanical element to position an energy conducting element according to aspects of the present invention.

As illustrated in FIG. 6, the adjustment system 300 may be an electromechanical system 310 that includes a motor 311 connected to a configuration 312 of one or more gears 313 coupled to the housing 110. The gears 313 in turn engage corresponding teeth 314 that are aligned parallel with the Z-axis and extend outwardly from the energy conducting element 111. As such, operation of the motor 311, via a user interface system 305, causes rotation of the gears 313 and corresponding movement of the teeth 314 and thus the energy conducting element 111 along the Z-axis.

To prevent the energy conducting element 111 from moving too far against the corneal surface 2A, a safety mechanism 116 may be employed as shown in FIG. 6. In particular, the energy conducting element 111 can move toward or against the corneal surface 2A until a stop 116B, which extends outwardly from, and moves with, the energy conducting element 111, makes contact with a corresponding stop extending inwardly from the housing 110. In other words, the stop 116A is positioned to block further movement of the block 116B and the energy conducting element 111 past a particular point along the Z-axis. In addition, FIG. 6 shows a bearing 110B that extends inwardly from the housing 110 and is positioned opposite the gear 113 to position the energy conducting element 111 within the passageway 110A of the housing 110. To ensure that the teeth 314 extending outwardly from the energy conducting element 111 properly engage the gear 113, a spring 110G may be employed to bias the energy conducting element 111 toward the gear 113. As described previously, any number of such bearings, or guiding elements, 110B may be employed within the housing 110. As shown in FIG. 6, springs 110G may be employed with any of these bearings 110B.

Like other embodiments described herein, the electromechanical system 310 may be applied to cause applanation of the cornea 2 to ensure sufficient contact has been established between the energy conducting device 111, i.e., the distal contact surfaces 111E and 111F, and the corneal surface 2A. Alternatively, as shown in FIG. 5, a physical measurement device 340, such as a strain gauge, may be employed with the electromechanical system 310 to measure the amount of pressure being applied by the distal surfaces 111E and 111F against the cornea 2. When operation of the motor 311 drives the gears 313 to cause the energy conducting element 111 to apply a force on the cornea 2, the corresponding reaction force acting on the energy conducting element 111 and the gears 313 acting on the teeth 314 place the energy conducting electrode in a state of compression. The physical measurement device 340 measures the amount of compression and the measurement can be translated into the pressure being applied to the cornea 2. A threshold pressure measurement corresponding to a desired amount of contact between the energy conducting electrode 111 and the cornea 2 can be determined. In general, the threshold value corresponds to the first instance of constant and uniform application of pressure on the cornea 2. Therefore, once the measured pressure reaches this threshold value, further downward movement of the energy conducting element 111 against the corneal surface 2A is not necessary. As such, causing applanation of the cornea 2 is also not necessary. In addition, the physical measurement device 340 also enables the application of a certain pressure to be reliably and accurately reproduced.

Figure 7:
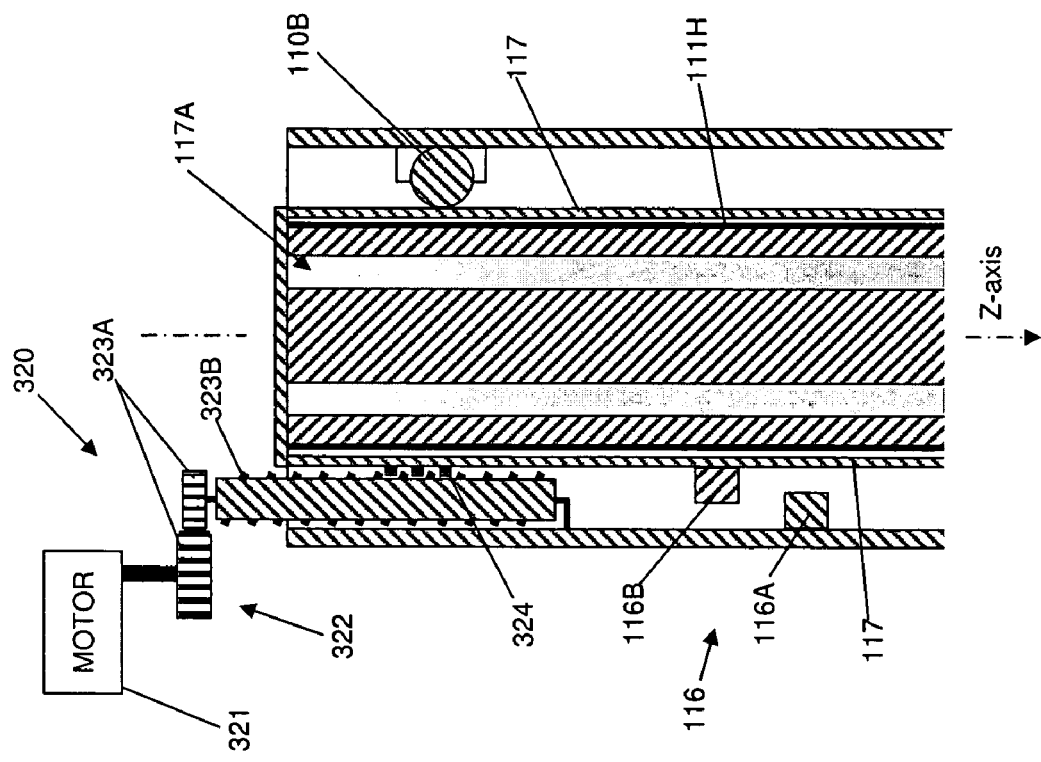
FIG. 7 illustrates a cross-sectional view of another embodiment that employs an electromechanical element to position an energy conducting element according to aspects of the present invention.

FIG. 7 illustrates another adjustment system 300 that employs an electromechanical system 320 including a motor 321 connected to an alternative configuration 322 of one or more gears 323 connected to the housing 110. FIG. 7 demonstrates that a variety of gear configurations may be employed according to aspects of the present invention. A gear configuration may be selected, for instance, according to the desired geometry of the assembled system. In particular, the configuration 322 in FIG. 7 includes gears 323A which cause a worm 323B to rotate about an axis parallel with the Z-axis. The worm 323B which is operably coupled to the housing 110 engages teeth 324 operably coupled to the energy conducting element 111. The teeth 324 are aligned parallel to the Z-axis and the rotation of the worm 323B causes the teeth 324 and the energy conducting element 111 to move along the Z-axis. The embodiment of FIG. 7 may employ a safety mechanism 116, as described previously. In addition, any number of such bearings, or guiding elements, 110B may be employed within the housing 110.

It is contemplated that additional intermediate structures may be employed to couple the energy conducting element 111 to the housing 110. For example, as shown in FIG. 7, rather than attaching the teeth 324 directly to an outer surface of the energy conducting element 111, the teeth 324 extend outwardly from an intermediate structure, or cylindrical structure, 117. The energy conducting element 111 is enclosed in a chamber 117A defined by the cylindrical structure 117, so that movement of the cylindrical structure 117 causes corresponding movement of the energy conducting element 111. The energy conducting element 111 may be clipped into, or otherwise coupled or attached to, the cylindrical structure 117. Of course, any connections to the energy conducting element 111, for example, with the electrical energy source (not shown), can be made through the wall(s) of the cylindrical structure 117. Advantageously, the energy conducting element 111 is not required to accommodate specific aspects of the adjustment system 300. In the embodiment of FIG. 7, the energy conducting element 111 does not have to include the teeth 324, as the teeth 324 are provided with the cylindrical structure 117. Because energy conducting elements 111 specially designed for the adjustment system 300 are not required, the applicator housing 110 is more easily compatible with different energy conducting elements 111. It is therefore contemplated that embodiments may include reusable applicator housings with replaceable interchangeable energy conducting elements 111.

Although the embodiments of FIGS. 6 and 7 employ electromechanical systems with gears, it is understood that other types of systems can be used to provide controlled movement of the energy conducting element 111 within the housing 110. For example, the electromechanical system 330 shown in FIG. 8 employs a piezoelectric system. In particular, a piezoelectric element, or material, 331 couples the energy conducting element 111 to the housing 110 and is connected to an electrical source 332. When the electrical source 332 is operated by the user interface system 305 to apply an electric field to the piezoelectric element 331, the piezoelectric element 331 expands or contracts along the Z-axis depending on the electric field. Because the energy conducting element 111 is coupled to the piezoelectric element 331, as shown in FIG. 8, the energy conducting element 111 is correspondingly moved in along the Z-axis.

Figure 9:
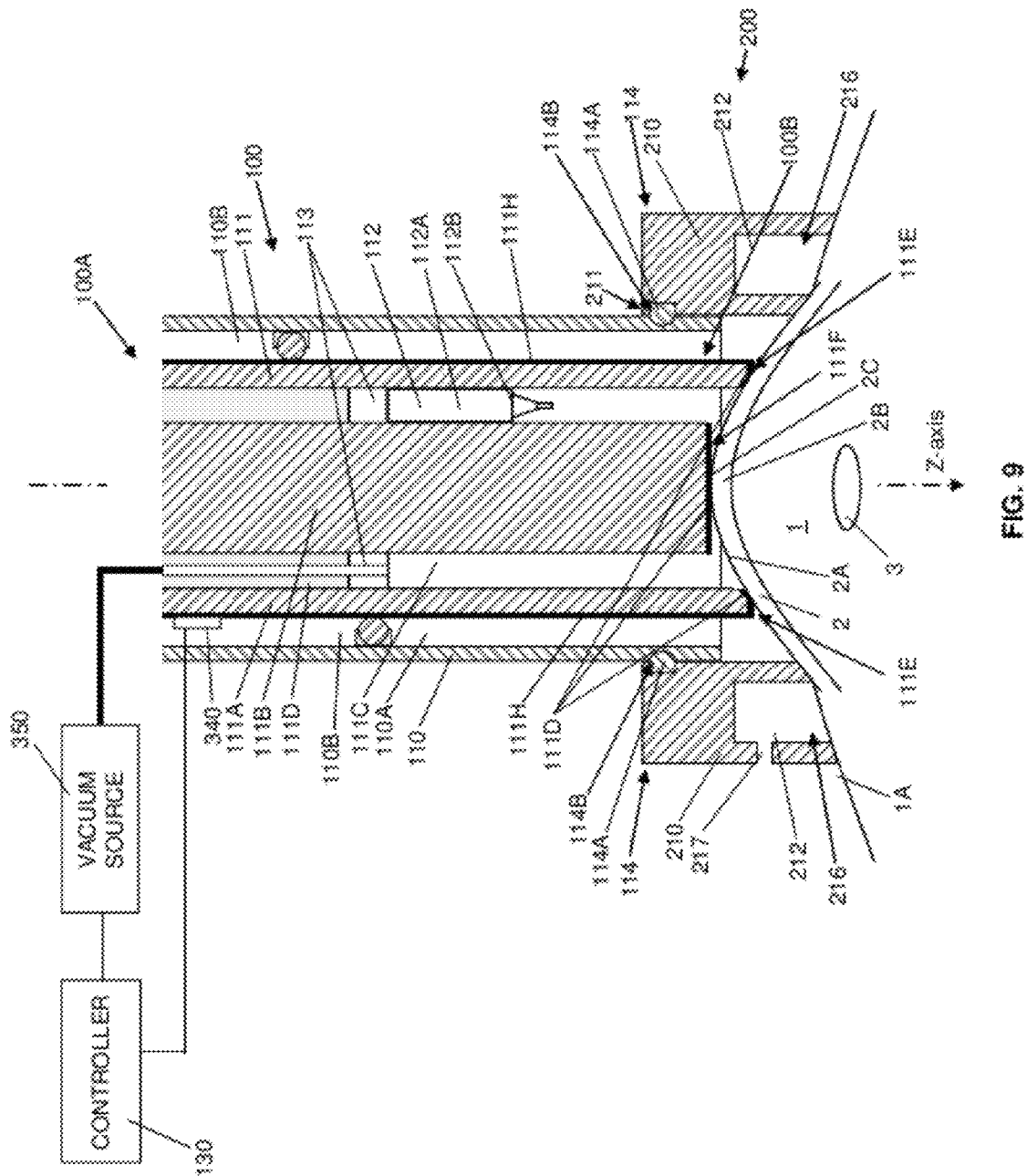
FIG. 9 illustrates a cross-sectional view of an embodiment that draws the cornea into contact with the energy conducting element according to aspects of the present invention.

It is also contemplated that the applicator 100 in alternative embodiments may draw the cornea 2 into desired contact with the energy conducting element 111. As FIG. 9 illustrates, the energy conducting element 111 may be positioned over the cornea 111. However, rather than moving the energy conducting element 111 against the corneal surface 2A, a vacuum source 350 is operated by a controller 130 to create a vacuum, or near vacuum, within the applicator 100 and draw or suction the corneal surface 2A into contact with the distal surfaces 111E and 111F. A physical measurement device 340 may be employed to indicate to the controller 130 that sufficient contact has been established. For example, if the physical measurement device 340 is a strain gauge, the strain gauge measures how much the energy conducting element 111 is being compressed as the cornea is drawn against the distal surfaces 111E and 111F by increasing suction levels from the vacuum source 350. Once the physical measurement device 340 signals that a desired threshold value has been achieved, the controller 130 maintains the level of vacuum to keep the cornea 2 in sufficient contact with the energy conducting electrode 111. It is noted that the controlled vacuum source 350 may be used in combination with an adjustment system that can position the energy conducting electrode 111 over the cornea 2 before the vacuum source 350 is operated.

Although the energy conducting element 111 in the previous embodiments conduct electrical energy to the cornea 2, it is also contemplated that other systems may be employed to apply energy to cause reshaping of the cornea. As shown in FIG. 10, another embodiment employs an applicator 400 that includes a housing 410 and an optical energy conducting element 411. The optical energy conducting element 411 passes through a passageway 410A in the housing 410 and is operably connected to an optical energy source 420, for example, via conventional optical fiber. Any number of bearings, or similar guiding structures, 410B may be employed to position the optical energy conducting element 411 within the housing 410. The optical energy source 420 may include a laser, a light emitting diode, or the like. The optical energy conducting element 411 extends to a distal end 400B from a proximal end 400A, where it is operably connected with the optical source 420. The optical energy conducting element 411 includes an optical fiber 411A. Thus, the optical fiber 411A receives optical energy from the optical energy source 420 at the proximal end 400A and directs the optical energy to the distal end 400B, where the cornea 2 of an eye 1 is positioned. A controller 430 may be operably connected to the optical energy source 420 to control the delivery, e.g. timing, of the optical energy to the optical conducting element 411. The optical energy conducting element 411 irradiates the cornea 2 with the optical energy and delivers energy for appropriately shrinking collagen fibers in the mid-depth region 2B of the cornea 2. As also illustrated in FIG. 10, the optical conducting element 411 may include an optical focus element 411B, such as a lens, to focus the optical energy and to determine the pattern of irradiation for the cornea 2. The distal end 400B of the optical conducting element 411, e.g., the optical focus element 411B, may include an eye contact surface 411C that makes constant and uniform contact with the cornea surface 2A. The application of energy to the cornea 2 may depend in part on the position of the optical conducting element 411 relative to the corneal surface 2A. As a result, to provide reliable application of energy to the cornea 2, embodiments ensure that the eye contact surface 411C is positioned to make contact with the corneal surface 2A. In this way, the relationship between the optical conducting element 411 and the cornea 2 is more definite and the resulting delivery of energy is more predictable. In some embodiments, sufficient contact is determined by causing an observable amount of flattening, or applanation, of the cornea, as shown in FIG. 10. In other embodiments, a physical measurement device, similar to device 340 above, may be employed to measure the amount of pressure being applied against the corneal surface 2A, so that applanation is not necessary to ensure that the eye contact surface 411C is in constant and uniform contact with the corneal surface 2A.

As shown in FIG. 10, the applicator 400 may also employ a coolant system 412 that selectively applies coolant to the corneal surface 2A. The coolant delivery system 412 as well as a coolant supply 413 may be positioned adjacent to the optical energy conducting element 411. The coolant system 412 may be operated, for example, with the controller 430 to deliver pulses of coolant in combination with the delivery of energy to the cornea 2. Applying the coolant in the form of pulses can help minimize the creation of a fluid layer between the optical energy conducting element 411 and the corneal surface 2A providing the advantages described previously.

As further illustrated in FIG. 10, the applicator 400 and the optical energy conducting element 411 are positioned over the cornea 2 by the positioning system 200 to deliver the optical energy to targeted areas of the cornea 2. The positioning system 200 is employed in the same manner similar to the previous embodiments. In particular, the positioning system 200 places the distal end 400B of the applicator 400 in a stable position over the cornea 2. For example, as described previously, a first coupling system 414 may be employed to couple the housing 410 to the attachment element 210 of the positioning system 200. The first coupling system 414 may include connecting elements 414A on the attachment element 210 that are received into cavities 414B on the applicator housing 410. Once the housing 410 is fully received into the attachment 210, the first coupling system 414 prevents the housing 410 from moving relative to the attachment element 210 along the Z-axis.

In addition, a second coupling system 415 is employed to couple the optical energy conducting element 410 to the housing 410. With the optical energy conducting element 411 positioned in the passageway 410A, the second coupling system 415 prevents the energy conducting element 411 from moving relative to the housing 410 along the Z-axis. For example, as illustrated in FIG. 10, the second coupling system 415 may include a connecting element 415A, such as a pin-like structure, which extends inwardly from the housing 410 into a cavity of a receiving structure 415B on the energy conducting element 411. Like the first coupling system 414, the second coupling system 415, of course, may employ other techniques for coupling the energy conducting element 411 to the housing 410. In general, the electrical conducting element 411, the housing 410, and the attachment element 210 are all fixed relative to each other while the attachment element 210 is attached to the corneal surface 2A. Accordingly, the optical conducting element 411 is able to apply constant pressure against the corneal surface 2A.

Alternatively, an automated adjustment system, as described previously, may be employed in a system using an optical energy conducting element 411. In particular, the automated adjustment system couples the optical energy conducting element 411 to the applicator housing 410, but allows electromechanically controlled movement of the optical energy conducting element 411 relative to the housing 410 along the Z-axis. With the housing 410 stably coupled to the attachment element 210 fixed to the eye surface 2A, the optical energy conducting element 411 may be moved into contact with the corneal surface 2A to provide a flattening pressure on the cornea.

Accordingly, embodiments according to aspects of the present invention provide a system and method for applying a thermokeratoplasty applicator to the cornea. In particular, embodiments provide a system and method for positioning the applicator over the cornea so that the applicator can cause the desired amount of flattening of a cornea and improve vision through the cornea. For example, embodiments may provide the applicator with an eye contact surface that is moved manually, electromechanically, etc. into contact with the corneal surface to physically flatten the cornea as energy is also delivered to the cornea. Advantageously, embodiments provide an improved system and method that facilitates handling and positioning of the applicator to achieve the desired reshaping of a cornea.

While various embodiments in accordance with the present invention have been shown and described, it is understood that the invention is not limited thereto. The present invention may be changed, modified and further applied by those skilled in the art. For example, although the applicators 200 and 400 in the examples above are separate elements received into the positioning system 200, the applicator 200 or 400 and the positioning system 200 may be combined to form a more integrated device. Thus, embodiments may include an integrated applicator housing and positioning system that receives and positions an energy conducting element against the cornea. Additionally, although the attachment element 210 in the embodiments above may be a vacuum device which is auctioned to the eye surface, it is contemplated that other types of attachment elements may be employed. For instance, the attachment element may be fixed to other portions of the head. Therefore, this invention is not limited to the detail shown and described previously, but also includes all such changes and modifications.

It is also understood that the Figures provided in the present application are merely illustrative and serve to provide a clear understanding of the concepts described herein. The Figures are not "to scale" and do not limit embodiments to the specific configurations and spatial relationships illustrated therein. In addition, the elements shown in each Figure may omit some features of the illustrated embodiment for simplicity, but such omissions are not intended to limit the embodiment.

What is claimed is:

1. A system for applying therapy to an eye, the system comprising:
    an applicator including a conducting element configured to direct energy from an energy source to an application end of the conducting element, the conducting element including an outer conductor and an inner conductor separated by a gap, the application end having an eye contact portion;
    a positioning system configured to receive the applicator and position the eye contact portion in engagement against a surface of an eye, the engagement creating a contact pressure between the eye contact portion and a feature of the eye, and the applicator being configured to direct energy to the eye according to the engagement; and
    a coupling system including:
        a measurement device operable to measure the contact pressure between the eye contact portion and the feature of the eye and generate a first signal indicative of the measured contact pressure,
        a controller configured to receive, from the measurement device, the first signal indicative of the measured contact pressure between the eye contact portion, analyze the first signal, and generate a second signal based on the analysis of the first signal, and
        an electromechanical adjustment system configured to move, relative to the positioning system, the outer conductor and the inner conductor within the positioning system in response to the second signal received from the controller.

2. The system according to claim 1, wherein the engagement is configured to cause applanation of the feature of the eye.

3. The system according to claim 1, wherein the eye contact portion includes a planar surface.

4. The system according to claim 1, wherein the outer conductor and the inner conductor define the application end with the eye contact portion.

5. The system according to claim 4, wherein the eye contact portion includes an edge on the outer electrode that is beveled.

6. The system according to claim 1, wherein the engagement is configured to cause the surface of the eye to be drawn into contact with the eye contact portion.

7. The system according to claim 6, further comprising a vacuum source configured to draw the surface of the eye into the engagement with the eye contact portion.

8. The system according to claim 1, wherein the applicator includes a housing and the conducting element is disposed within the housing.

9. The system according to claim 8, wherein the coupling system is configured to controllably move the conducting element relative to the housing.

10. The system according to claim 8, wherein the eye contact portion of the conducting element extends from a distal end of the housing.

11. The system according to claim 8, further comprising a second coupling system for fixedly coupling the housing to the positioning system.

12. The system according to claim 1, wherein the electromechanical device includes a motorized gear configuration.

13. The system according to claim 1, wherein the electromechanical device includes a piezoelectric element.

14. The system according to claim 1, wherein the positioning system includes an adjustable attachment element configured to be removably attached to the surface of the eye, the attachment element centering the conducting element over the feature of the eye.

15. The system according to claim 14, wherein the attachment element includes a vacuum ring configured to create a vacuum connection with the surface of the eye.

16. The system according to claim 14, wherein the positioning system further includes a receiving element operably coupled to the attachment element and movable relative to the attachment element, the receiving element being configured to receive the applicator, and further comprising a movement element controlling the movement of the receiving element relative to the attachment element.

17. The system according to claim 1, wherein the coupling system is configured to transduce rotational movement provided by a motor into linear movement of the conducting element.

18. The system according to claim 1, wherein the measurement device is a strain gauge.

19. A method for applying therapy to an eye, the method comprising:
    attaching a positioning system to a surface of an eye, the positioning system having an aperture providing access to a feature of the eye within the aperture;
    coupling a conducting element to the positioning system such that the conducting element is received in the aperture of the positioning system and positioned relative to the feature of the eye, the conducting element being operably connected to an energy source, the conducting element having an application end for directing energy to the eye, the application end having an eye contact portion;
    with the conducting element coupled to the positioning system, moving the conducting element in at least a first direction relative to the positioning system, the first direction being generally perpendicular to an axis of the aperture;
    measuring, using a measurement device, an amount of contact between the eye contact portion and the feature of the eye;

providing a first signal indicative of the measured amount of contact to a controller;

providing a second signal from the controller to an adjustment system based on the first signal;

moving the eye contact portion in a second direction relative to the positioning system, using the adjustment system controlled by the controller, based on the second signal, the second direction being generally parallel to the axis of the aperture; and directing energy from the energy source to the feature of the eye via the application end.

20. The method according to claim 19, further comprising moving the eye contact portion into engagement with the feature of the eye.

21. The method according to claim 19, further comprising drawing the feature of the eye into engagement with the eye contact portion.

22. The method according to claim 21, wherein the step of drawing the feature of the eye comprises operating a vacuum source to suction the feature of the eye into engagement with the eye contact portion.

23. The method according to claim 19, further comprising positioning the conducting element into an applicator housing having the adjustment system.

24. The method according to claim 23, wherein the moving the eye contact portion includes operating an electromechanical device.

25. The method according to claim 19, further comprising determining, using the controller, whether a specified amount of contact between the eye contact portion and the feature of the eye has been established.

26. The method according to claim 25, wherein the step of determining whether a specified amount of contact has been established comprises causing applanation of the feature of the eye.

27. The method according to claim 25, wherein the step of measuring the amount of contact comprises operating a strain gauge.

28. The method according to claim 25, further comprising stopping, using the controller, the moving of the eye contact portion in response to the controller determining that the specified amount of contact between the eye contact portion and the feature of the has been established.

29. The method according to claim 19, wherein the eye contact portion is moved relative to the positioning system by an electromechanical device.

30. The method according to claim 29, further comprising providing a signal from the controller to the electromechanical device, the electromechanical device moving the eye contact portion relative to the positioning system in response to the signal being received by the electromechanical device.

31. The method according to claim 29, wherein the electromechanical device is configured to transduce rotational movement provided by a motor into linear movement of the eye contact portion.

* * * * *